US012612629B2

(12) United States Patent
Chang et al.

(10) Patent No.: US 12,612,629 B2
(45) Date of Patent: Apr. 28, 2026

(54) DUCHENNE MUSCULAR DYSTROPHY-RELATED EXONIC SPLICING ENHANCER, sgRNA AND GENE EDITING TOOL, AND APPLICATIONS

(71) Applicant: WESTLAKE UNIVERSITY, Hangzhou (CN)

(72) Inventors: Xing Chang, Hangzhou (CN); Jia Li, Hangzhou (CN); Han Qiu, Hangzhou (CN)

(73) Assignee: WESTLAKE UNIVERSITY, Hangzhou (CN)

( * ) Notice: Subject to any disclaimer, the term of this patent is extended or adjusted under 35 U.S.C. 154(b) by 547 days.

(21) Appl. No.: 18/043,874

(22) PCT Filed: Sep. 30, 2020

(86) PCT No.: PCT/CN2020/119361
§ 371 (c)(1),
(2) Date: Mar. 2, 2023

(87) PCT Pub. No.: WO2022/047876
PCT Pub. Date: Mar. 10, 2022

(65) Prior Publication Data
US 2023/0287419 A1 Sep. 14, 2023

(30) Foreign Application Priority Data
Sep. 2, 2020 (CN) .......................... 202010909759.7

(51) Int. Cl.
*C12N 15/113* (2010.01)
*A61P 21/00* (2006.01)
*C07K 14/47* (2006.01)
*C12N 15/86* (2006.01)

(52) U.S. Cl.
CPC ............ *C12N 15/113* (2013.01); *A61P 21/00* (2018.01); *C07K 14/4708* (2013.01); *C12N 15/86* (2013.01); *C12N 2750/14143* (2013.01)

(58) Field of Classification Search
CPC ................. C12N 15/113; C12N 15/86; C12N 2750/14143; C12N 2310/20; A61P 21/00; A61P 9/00; C12Y 305/04005; C07K 2319/00
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

2020/0390042 A1* 12/2020 Taylor, Jr. ............ A01G 25/023
2022/0306573 A1* 9/2022 Zhang ................... C07C 317/28

FOREIGN PATENT DOCUMENTS

| CN | 102171342 A | 8/2011 | |
| CN | 104203289 A | 12/2014 | |
| CN | 105658805 A | 6/2016 | |
| CN | 109295053 A | 2/2019 | |
| CN | 110835632 * | 2/2020 | ........... C12N 15/113 |
| EP | 1191098 A2 | 3/2002 | |
| JP | 2016521555 A | 7/2016 | |
| WO | 2014197748 A2 | 12/2014 | |
| WO | WO-2018129296 A1 * | 7/2018 | .............. A61P 21/04 |
| WO | 2019152609 A1 | 8/2019 | |
| WO | 2020118246 A1 | 6/2020 | |

OTHER PUBLICATIONS

Yuan et al.(Molecular Cell, vol. 72, pp. 1-15 (2018)) (Year: 2018).*
Yuan, Juanjuan et al.; "Genetic Modulation of RNA Splicing with a CRISPR-Guided Cytidine Deaminase"; Molecular Cell; vol. 72, 1-15. e1-e7; Oct. 18, 2018; pp. 1-23.
Grieger, Joshua C. et al.; "Production and characterization of adeno-associated viral vectors"; Nature Protocols; vol. 1, No. 3; Nov. 9, 2016; pp. 1412-1428.
Long, Chengzu et al.; "Correction of diverse muscular dystrophy mutations in human engineered heart muscle by single-site genome editing"; Science Advances I Research Article; vol. 4; Jan. 31, 2018; 1-11.
Qiu, Han et al., "Efficient exon skipping by base-editor-mediated abrogation of exonic splicing enhancers", Cell Reports, vol. 42, No. 11, Nov. 28, 2023, Available online Oct. 30, 2023, pp. 1-18.

* cited by examiner

*Primary Examiner* — Jane J Zara

(74) *Attorney, Agent, or Firm* — NKL Law; Bin Lu; Allen Xue

(57) ABSTRACT

A duchenne muscular dystrophy-related exonic splicing enhancer, sgRNA and gene editing tool can be applied in the preparation of drugs for treating duchenne muscular dystrophy. The gene editing tool designed on the basis of cytosine deaminase AID mutants and Cas9 mutants can perform site-specific modification on a mammalian genome by using an adeno-associated virus (AAV) as a vector. By optimizing an encoding nucleic acid sequence and an element composition structure of the editing tool, site-specific targeted modification of mammalian genetic material DNA can be efficiently achieved; and by performing targeted genetic manipulation on the nucleic acid sequence carrying disease mutations, a pathogenic mutation cannot be retained in a mature protein amino acid sequence or the pathogenic mutation cannot perform its function, so that the purpose of treating various gene mutation type genetic rare diseases is achieved, and the advantages of high efficiency, safety and stability are achieved.

8 Claims, 8 Drawing Sheets

Specification includes a Sequence Listing.

FIG. 3 Continued

DUCHENNE MUSCULAR DYSTROPHY-RELATED EXONIC SPLICING ENHANCER, sgRNA AND GENE EDITING TOOL, AND APPLICATIONS

INCORPORATION OF SEQUENCE LISTING

This application contains a sequence listing submitted in Computer Readable Form (CRF). The CFR file containing the sequence listing entitled "PBA408-0108_ST25.txt", which was created on Mar. 2, 2023, and is 48,312 bytes in size. The information in the sequence listing is incorporated herein by reference in its entirety.

TECHNICAL FIELD

The invention belongs to the field of gene therapy, and relates to the modified treatment of a Duchenne muscular dystrophy related exon splicing enhancer, sgRNA and gene editing tool in mammals (experimental animal models and human patients) for pathogenic mutations of gene mutation type genetic diseases. In particular, it relates to the gene editing therapy of Duchenne muscular dystrophy (DMD) in mouse models and human patients.

BACKGROUND

According to the definition of the World Health Organization (WHO), rare diseases are unusual diseases that affect 0.065%-0.1% of the total population in a certain region. The pathogenesis of such diseases is often difficult to find, and lacks targeted treatment drugs, which brings great harm to the health of patients and brings great burden to their families and society. Due to the extremely high population base in China, the absolute number of rare diseases cannot be ignored. In recent years, it has attracted the attention of scientific researchers and clinical experts. In May 2018, five departments, including the China's National Health Commission, the Ministry of Science and Technology, the Ministry of Industry and Information Technology, the State Drug Administration and the State Administration of Traditional Chinese Medicine, jointly released the catalog of the First Batch of Rare Diseases, in which 121 diseases were listed. It indicates that rare diseases have received further attention and concern in China.

The pathogenesis of rare diseases is often due to genetic mutations, resulting in complex multiple clinical disease manifestations. Due to the limitations of diagnostic means, patients who show clinical symptoms early in the course of the disease are generally classified as a single disease, and after long-term treatment but have not been improved, they will be further judged as difficult undiagnosed diseases. Therefore, it is urgent to carry out relevant research on difficult undiagnosed diseases/rare diseases, including but not limited to: investigation of pathogenic mechanism, optimization of diagnostic means, tracking of pathogenesis, screening of drug targets and development of targeted gene drugs combined with gene editing technology. At the same time, the discovery and improvement of animal models of special rare diseases can also improve the comprehensive understanding of rare diseases and the innovation of targeted drugs. The present invention takes Muscular Dystrophy, a rare disease that has been clinically discovered earlier but lacks effective treatment methods for a long time, as the entry point. The present invention takes Duchenne Muscular Dystrophy (DMD) as the research object, combines with the newly discovered mouse model, develops and optimizes the gene therapy for the disease, and applies the gene therapy method to the human genome sequence.

Duchenne muscular dystrophy (DMD) is an X-chromosome genetic disorder that can be detected in approximately one in every 4,000 newborn males, and is caused by the loss of expression of Dystrophin protein due to genetic mutations. For DMD patients, tissue damage and dysfunction of the heart muscle is the most deadly threat. For a long time, there was no effective treatment for DMD, and the treatment that could be given clinically was limited to symptom relief: for example, angiotensin inhibitors were used to relieve the discomfort caused by myocardial degeneration, the drugs including Perindopril, and a variety of 1ol beta receptor blockers. At the same time, with the improvement of medical methods, interventional treatment also helps to relieve the symptoms of DMD patients, including cardiac circulatory assistance system and respiratory assistance system. However, these treatments cannot substantially improve the quality of life of DMD patients and prolong the life of DMD patients. Progressive deterioration of heart function is still the most important cause of death in DMD patients.

With the continuous progress of molecular biology, combined with clinical data analysis, it has been found that a group of patients with the same mutation in the gene encoding Dystrophin protein do not show the same severe pathological process as DMD patients. Such group of patients is called Bayes muscular dystrophin (BMD) patients. The mutations in the Dystrophin gene they carried will not cause the destruction of the open reading frame of the intact protein, so they can produce a Dystrophin protein that has a certain biological function and do not show severe cardiac dysfunction or other deficiencies in muscle function. Compared with the severe pathological process of DMD patients, BMD patients will not be significantly affected in their life expectancy and can almost resume their daily life as normal people.

The emergence of such BMD patients has given researchers an inspiration whether it is possible to induce the skipping of exons with mutations in DMD patients without affecting the protein reading frame, thereby producing a nearly full-length Dystrophin protein for the treatment of DMD patients. This idea has been put into practice in recent years, and there are now a variety of Exons with mutations can be treated with this regimen, and several of which have been approved for clinical trials. By the end of 2019, only a limited number of specific drugs for DMD had been approved for marketing worldwide. Among them, Sarepta Therapeutics is a biotechnology company focused on developing precision gene therapies to treat rare diseases. Golodirsen developed by them was on the market on Dec. 12, 2019 with accelerated approval by the US FDA for the treatment of DMD patients diagnosed with a gene mutation of the exon 53 skipping. It is estimated that about 8% of DMD patients carry this mutation. The essence of Golodirsen is an antisense oligonucleotide that works by targeting the sequence of dystrophin protein. Therefore, drugs designed for other mutation sites are still a huge gap at present. At present, including DMD-targeted drugs that have entered clinical trials, competition is fierce, but the demand for drugs is still huge in worldwide. Currently, there are 5 drugs on the market for DMD, 6 drugs are in the clinical phase III trial stage, 19 drugs are in the clinical phase II stage, and 5 drugs have just entered the clinical phase I trial stage. It should be noted that in human DMD patients, these drugs are only suitable for one type of patient with a specific mutation, and for other DMD patients, there is still a lack of sufficient targeted treatment drugs. Eteplirsen developed by Sarepta Therapeutics is an antisense phosphorodiamidate morpholino oligomer (PMO) therapeutic agent, and is the first marketed drug (2016) for the treatment of DMD of the company. However, these currently marketed drugs often have the disadvantages of low treatment efficiency, the need for continuous administration, and extremely expensive price. However, gene editing therapy regimen can directly target the pathogenic mutations of genetic diseases with gene mutation. Once edited, it can fundamentally cure the disease, which has great advantages.

Not only for the type of DMD disease, the use of gene editing tools to treat rare genetic diseases is extremely rare worldwide.

SUMMARY OF THE INVENTION

The object of the present invention relates to targeting gene mutation type genetic rare diseases, and is to provide a Duchenne muscular dystrophy-related exon splicing enhancer, sgRNA and gene editing tool as drugs for gene editing therapy in vivo in mammals (animal models of diseases and human patients).

In the first aspect, the present invention provides a Duchenne muscular dystrophy-related exon splicing enhancer, which is an exon splicing enhancer element targeting the human DMD gene Exon51, wherein the nucleotide sequence of that comprises:

1) The sequence as shown in SEQ ID NO: 21 and the reverse complementary sequence thereof.
2) The sequence as shown in SEQ ID NO: 22 and the reverse complementary sequence thereof.
3) The sequence as shown in SEQ ID NO: 23 and the reverse complementary sequence thereof.
4) The sequence as shown in SEQ ID NO: 24 and the reverse complementary sequence thereof.

By changing or blocking the above-mentioned exon splicing enhancer (ESE) and other elements, the DMD gene Exon51 can be induced to skip, thereby realizing gene editing therapy in mammals. For example, CRISPR nuclease can destroy the structure of ESE through insertions and deletions (Indels) introduced by double-strand breaks of DNA; Antisense oligonucleotide (ASO) prevents retention into the final protein amino acid sequence by targeting the corresponding element position of pre-mRNA in the cell.

In the second aspect, the present invention also provides a Duchenne muscular dystrophy-related single-stranded guide RNA (sgRNA) that may target a particular genome, wherein the sequence of the sgRNA comprises:

sgRNA targeting the mouse mutation site Dmd-E4 with the nucleotide sequence as shown in SEQ ID NO: 4.
sgRNA targeting the human DMD gene Exon50 with the nucleotide sequence as shown in SEQ ID NO: 7.
sgRNA-1 targeting the human DMD gene Exon51 with the nucleotide sequence as shown in SEQ ID NO: 8.
sgRNA-2 targeting the human DMD gene Exon51 with the nucleotide sequence as shown in SEQ ID NO: 9.
sgRNA-3 targeting the human DMD gene Exon51 with the nucleotide sequence as shown in SEQ ID NO: 10.
sgRNA-4 targeting the human DMD gene Exon51 with the nucleotide sequence as shown in SEQ ID NO: 11.
sgRNA-5 targeting the human DMD gene Exon51 with the nucleotide sequence as shown in SEQ ID NO: 12.
sgRNA-6 targeting the human DMD gene Exon51 with the nucleotide sequence as shown in SEQ ID NO: 13.
sgRNA-7 targeting the human DMD gene Exon51 with the nucleotide sequence as shown in SEQ ID NO: 14.

sgRNA-8 targeting the human DMD gene Exon51 with the nucleotide sequence as shown in SEQ ID NO: 15.
sgRNA-9 targeting the human DMD gene Exon51 with the nucleotide sequence as shown in SEQ ID NO: 16.
sgRNA-10 targeting the human DMD gene Exon51 with the nucleotide sequence as shown in SEQ ID NO: 17.
sgRNA-11 targeting the human DMD gene Exon51 with the nucleotide sequence as shown in SEQ ID NO: 18.
sgRNA-12 targeting the human DMD gene Exon51 with the nucleotide sequence as shown in SEQ ID NO: 19.
sgRNA-13 targeting the human DMD gene Exon51 with the nucleotide sequence as shown in SEQ ID NO: 20.
The sgRNA is combined with a gene editing tool and can be used in the preparation of drugs for the treatment of Duchenne muscular dystrophy.

In the third aspect, the present invention also provides a Duchenne muscular dystrophy-related gene editing tool, comprising a fusion protein of cytosine deaminase and Cas9 mutant, the sgRNA of claim 2 and a vector. The vector is a commonly used biological plasmid, such as AAV vector plasmid, pCDNA3.1 plasmid, etc.

Further, cytosine deaminase may be AID, apobec, etc., preferably, cytosine deaminase is AID. The amino acid sequence and nucleic acid sequence of the fusion protein of AID and Cas9 mutant are as shown in SEQ ID NO: 1 and SEQ ID NO: 2, respectively.

Further, the gene editing tool is packaged by adenoassociated viral (AAV) vector. Adeno-associated virus (AAV) can deliver nucleic acid sequences expressing AID-Cas9 fusion protein and sgRNA to target cells, so that it can express proteins with DNA editing function and sgRNA molecules with guidance function in the cell, wherein sgRNA can guide AID-Cas9 fusion protein to specific genomic sites in target cells to induce modification of pathogenic mutations, and inactivate them to achieve the purpose of treating diseases.

Further, the promoter of the adeno-associated viral vector (AAV) is a Syn100 promoter or a promoter designed based on ck8a, mhck7, etc.

Further, the nucleotide sequence of the adeno-associated viral vector (AAV) is shown in SEQ ID NO: 3.

The present invention also provides a use of the abovementioned gene editing tool in the preparation of drugs for the treatment of Duchenne muscular dystrophy.

The beneficial effects of the present invention are:

Taking the pathogenic mutations carried by DMD mouse models and pathogenic mutations carried by human DMD patients as examples, the present invention used adenoassociated virus (AAV) to achieve the treatment of DMD mouse models in vivo by designing and constructing a gene editing tool. At the same time, a gene editing regimen was designed for the pathogenic mutations of human DMD patients, and the modification of pathogenic mutations was realized at the cellular level. The present invention provides an innovative treatment method for gene mutation type genetic rare diseases which is expected to achieve breakthrough therapeutic effects for many genetic rare diseases.

DETAILED DESCRIPTION

Taking the pathogenic mutations carried by DMD mouse models and pathogenic mutations carried by human DMD patients as examples, the present invention achieved the modification of pathogenic mutations by designing and constructing gene editing tools. The present invention is further described below combining specific examples and accompanying drawings:

Example 1 AAV Virus Carrying Gene Editing Tools

Figure 1:
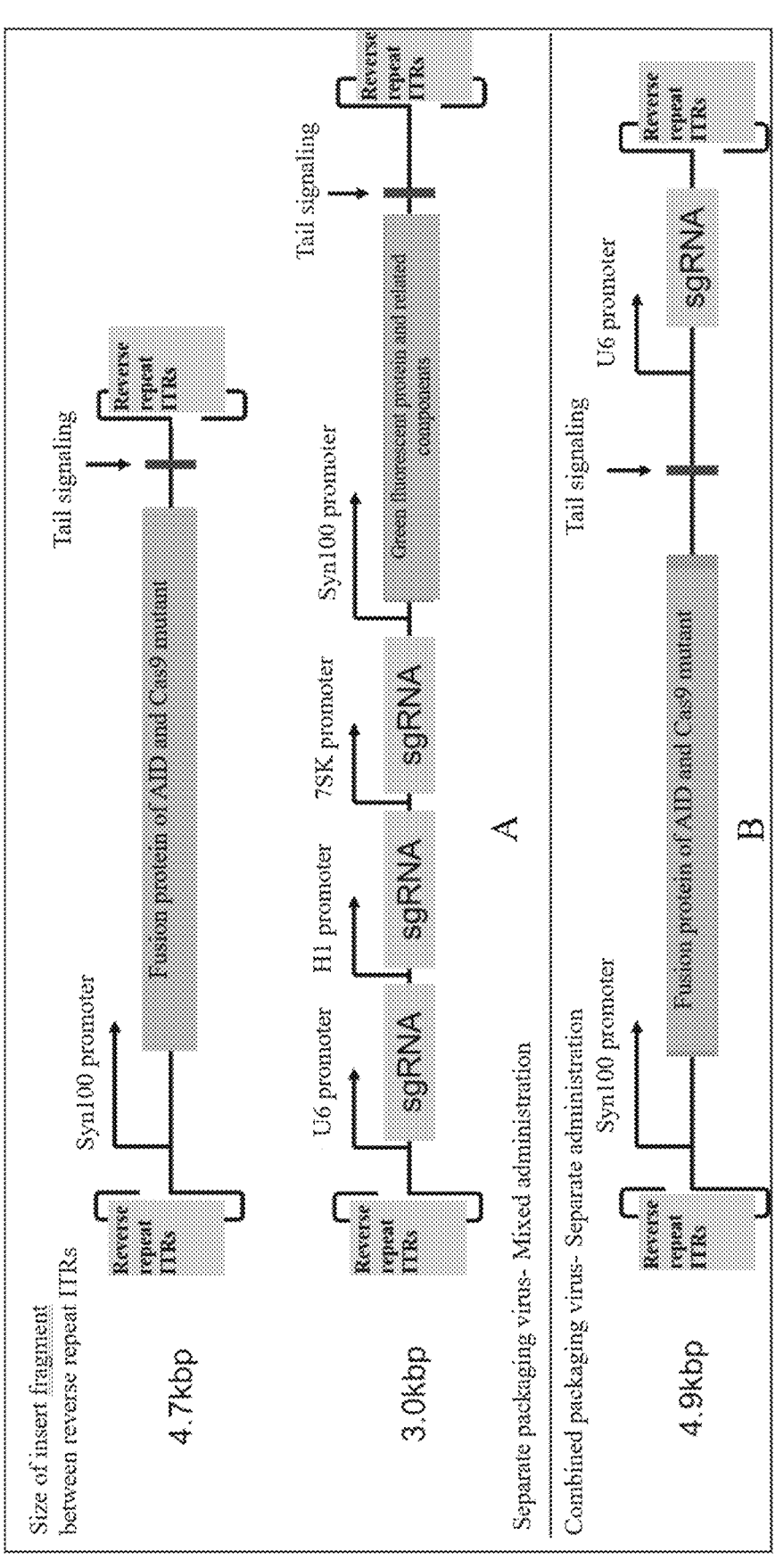
FIG. 1 shows the functional elements including the gene editing tool, wherein A shows a separate packaging virus and B shows a combined packaging virus.

The gene editing tool designed according to the present invention is shown in FIG. 1. Taking AID as an example, we cloned the corresponding sequence into the AAV plasmid, including the following steps:

First, pAAV2 backbone vectors (purchased from addgene, but not limited to it) were double-digested based on the digestion sites of XhoI and NotI. At the same time, the amino acid sequence of AID and Cas9 fusion protein in gene editing tools was designed. The amino acid sequence and nucleic acid sequence of AID and Cas9 fusion proteins are shown in SEQ ID NO: 1 and SEQ ID NO: 2, respectively. After codon optimization, double-stranded DNA fragment was directly synthesized, and it was connected with a Syn100 promoter, a tail signaling element and other elements to AAV backbone vector to obtain an AAV vector plasmid expressing AID-Cas9 mutant fusion protein, and the sequence of that is as shown in SEQ ID NO: 3.

Figure 3:
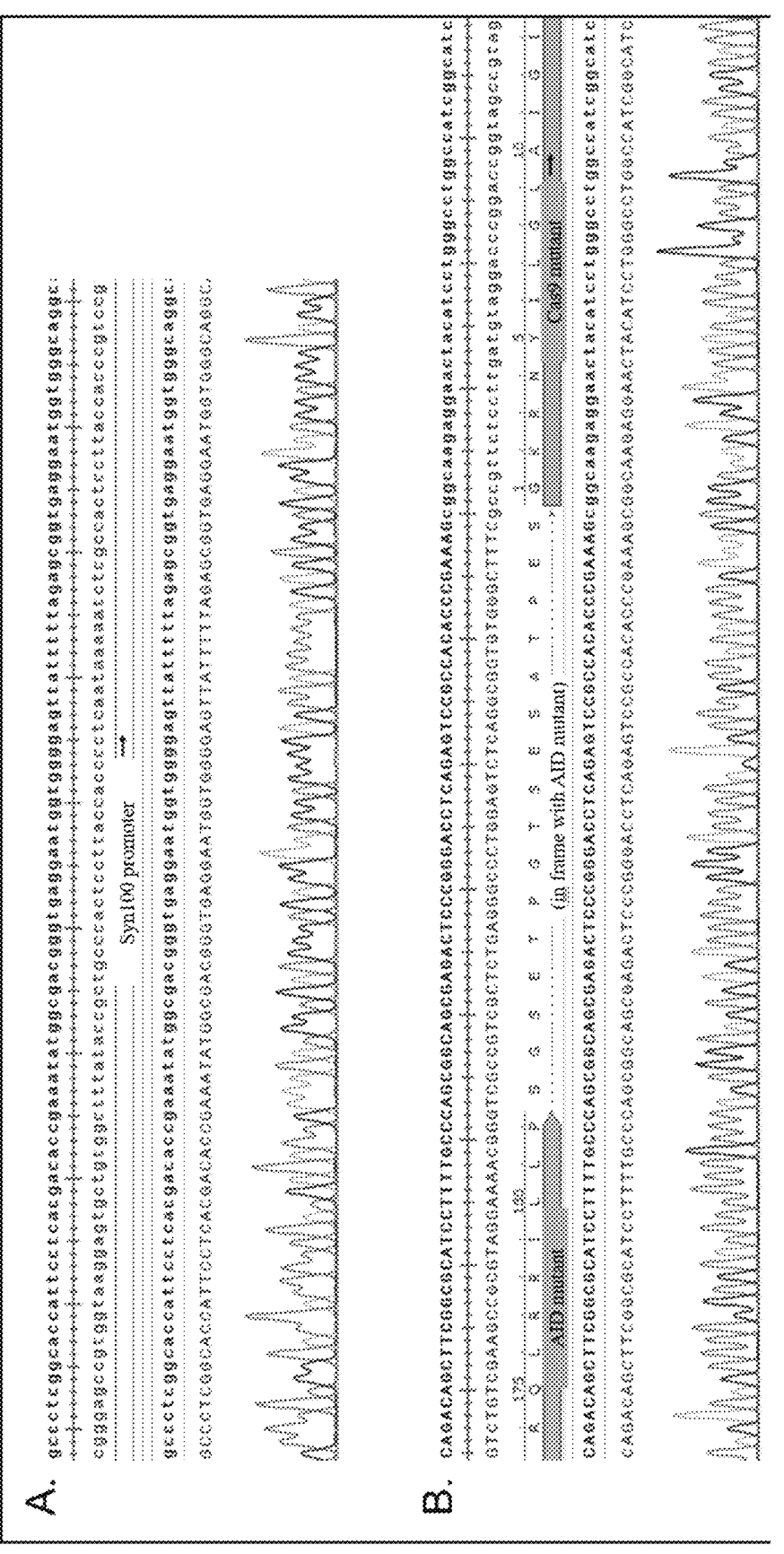
FIG. 3 shows the partial sequencing results of AAV plasmids; wherein, A shows the sequencing alignment result of the Syn100 promoter; B shows the sequencing alignment result of the AID and Cas9 mutant fusion protein; C shows the sequencing result of the U6 promoter.

In addition, by primer synthesis and PCR, the sequences of the U6 promoter, H1 promoter and 7SK promoter can be connected with sgRNA that identifies the splicing site of the pathogenic mutation exon, and the Syn100 promoter and tail signaling element were used to express green fluorescent protein and related components to increase protein expression tags and help improving gene editing efficiency. In addition, gene editing tool can be constructed using an AAV plasmid with combined packaging virus. On the basis of AID and Cas9 fusion protein expression elements, the U6 promoter was connected with sgRNA targeting the pathogenic mutant exon splicing site to construct an AAV plasmid vector with a 4.9 kbp insertion sequence. Partial results for related plasmid cloning are shown in FIG. 3 below.

After constructing the completed AAV vector plasmid, according to previous literature [Grieger, J., Choi, V. & Samulski, R. Production and characterization of adeno-associated viral vectors. Nat Protoc 1, 1412-1428 (2006).], AAV virus of a serotype AAV9 was packaged and purified with a titer of $1 \times 10^{13}$ v·g·/mL. The separate packaging virus was mixed proportionally when used, and the combined packaging virus can be directly used for in vivo treatment.

Example 2: In Vivo Treatment of DMD Model Mice Using AAV Carrying Gene Editing Tools A new DMD mouse disease model Dmd-E4 with abnormal cardiac function was selected in the present example.

The model can be purchased from Jiangsu Jicui Pharma Biotechnology Co., Ltd., but not limited to it. Dmd-E4 showed cardiac hypertrophy, fibrosis and other phenotypes in the heart at 6-8 weeks, and showed severe cardiac degeneration at about 8 months. This process well mimiced the cardiac pathological process of DMD patients. For this model, cytosine deaminase and Cas9 were used to design gene editing tools to target exons carrying pathogenic mutations, and mutations near the 5' splicing sites of that were induced to make them skip, and maximize the preservation of Dystrophin protein expression and restore its biological functions without affecting the open reading frame of the protein.

Specifically, the method of Example 1 was used to construct a gene editing tool, wherein the sgRNA sequence designed for the Dmd-E4 mouse mutation site is as shown in SEQ ID NO: 4, and the AAV vector plasmid that expressing the sgRNA targeting the Dmd-E4 mouse mutation site was obtained, and its sequence is shown in SEQ ID NO: 5. The corresponding sequence containing the AID-Cas9 fusion protein and the sgRNA targeting Dmd-E4 mice in the same AAV vector plasmid is shown in SEQ ID NO: 6.

Figure 2:
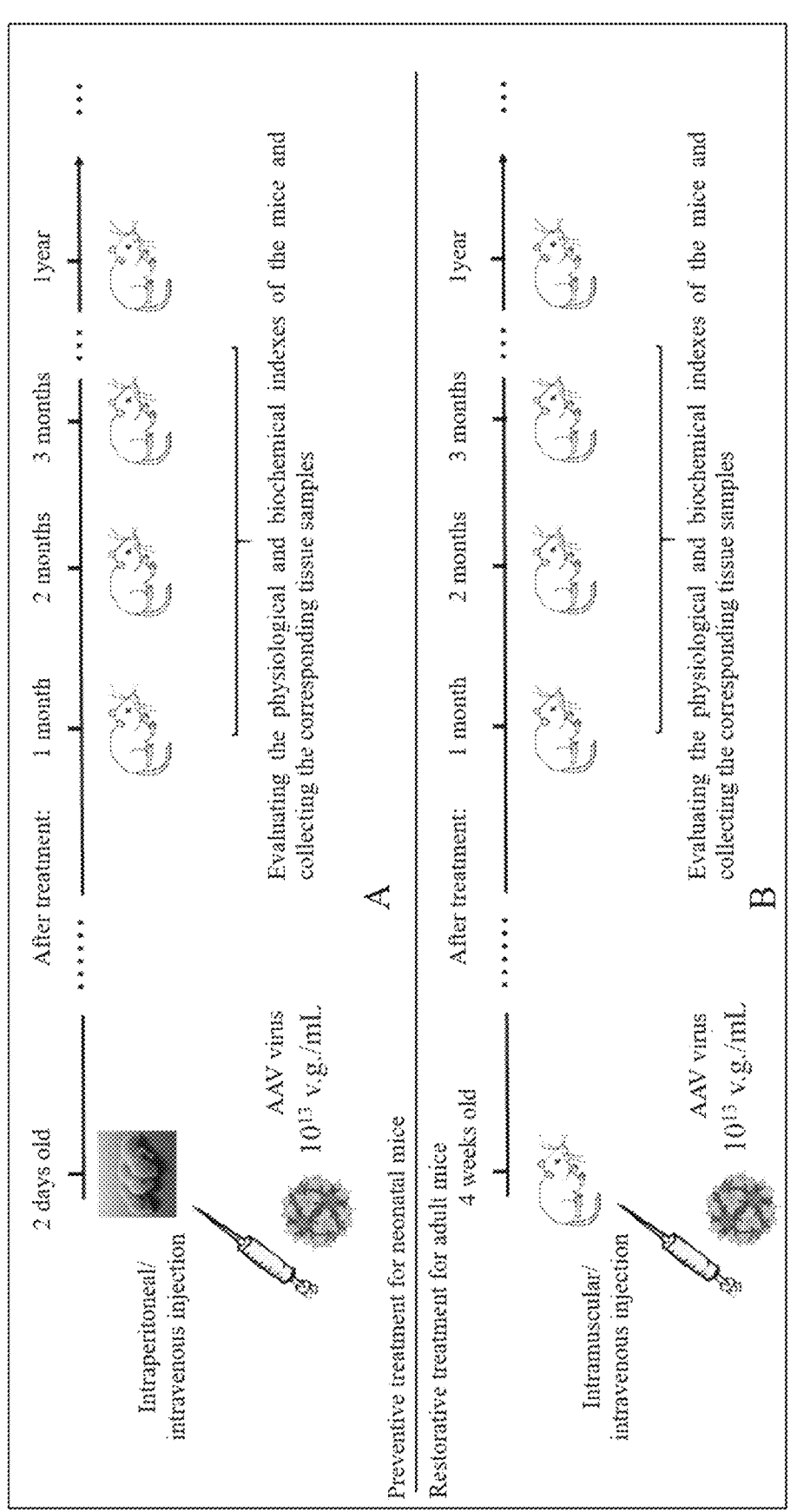
FIG. 2 shows the treatment flow chart of the novel DMD mouse disease model Dmd-E4, wherein A shows preventive treatment for neonatal mice and B shows restorative treatment for adult mice.

Serotype AAV9 was selected for viral synthesis and purification, and Dmd-E4 mice were treated according to the two regimens of preventive treatment for neonatal mice and restorative treatment for adult mice, as shown in FIG. 2.

(A) Gene Therapy for Neonatal Mice

Grouping: Homozygous KO male and female Dmd-E4 mice were mated. After the female mice were pregnant, the male and female mice were caged, and the pregnant female mice were observed every two days to confirm whether they gave birth. After the birth of the newborn Dmd-E4 mice, the sex was observed, then 3-5 male mice were selected as the experimental group, and the other 3-5 male mice were as the negative control group.

Administration: 50-75 µL of adeno-associated virus (AAV) carrying the gene editing tool (with a titer of $10^{13}$ v·g·/mL) was administered by intraperitoneal injection or facial intravenous injection, and control mice were given an equal volume of sterile PBS at the same time, and then they were housed normally with female mice.

Sampling and detection: When the mice grew to about 2 months, in addition to the experimental group and the control group, 3-5 WT male mice of the same age were taken, and the following treatment was performed at the same time: after anesthetizing the mouse, the function test of the tibial anterior muscle, echocardiogram detection and the like was first performed, and then cardiac arteriovenous blood was collected to sacrifice the mouse. The serum was separated by centrifugation and stored at −80° C., while myocardium, skeletal muscle, tibial anterior muscle, back muscle, liver, brain, kidney and other tissues were collected, and proteins, RNA, genomic DNA of that were extracted. Enough tissues were retained for immunofluorescence staining, hematoxylin eosin staining, etc.

Figure 4:
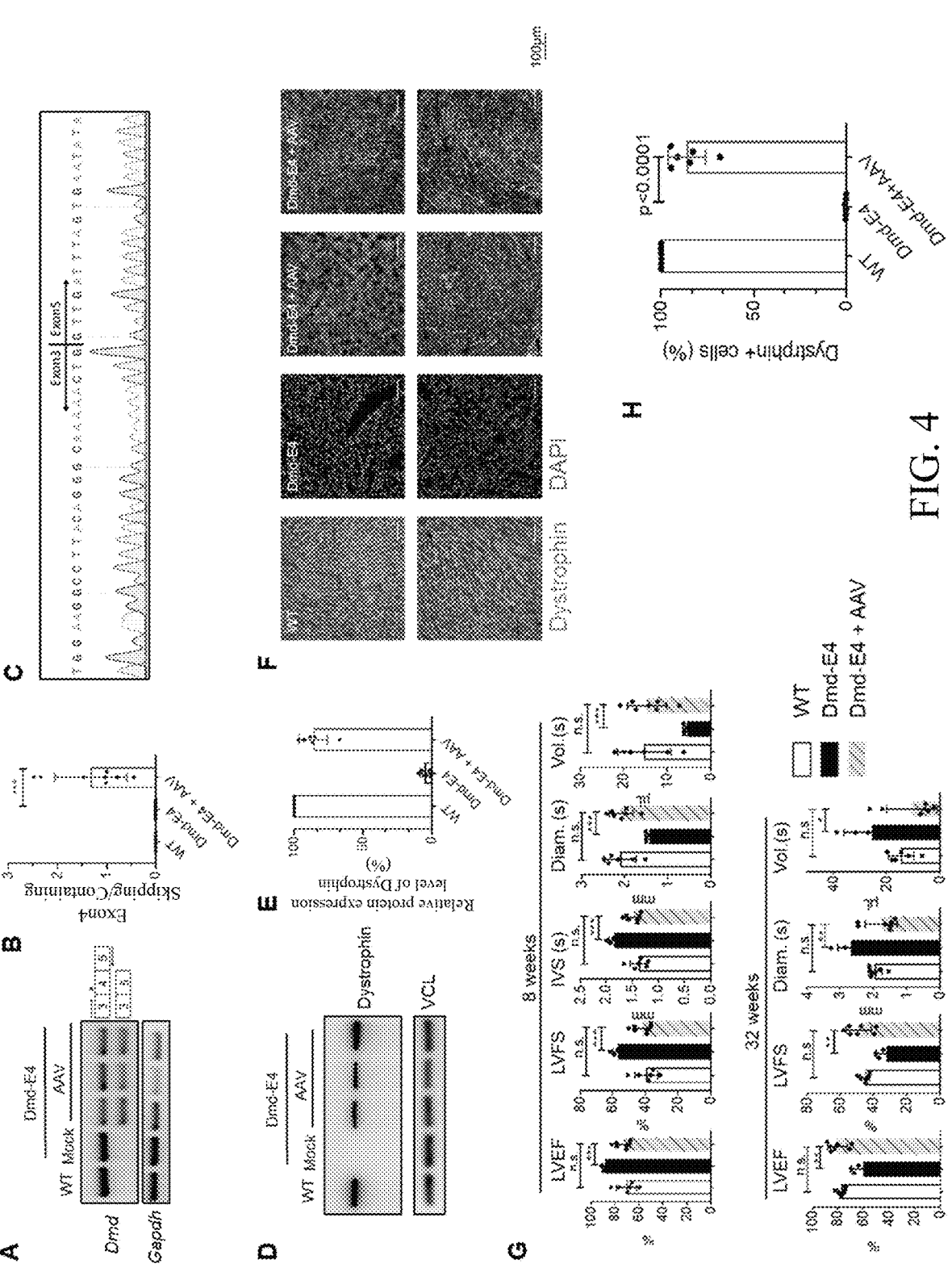
FIG. 4 shows the results diagram that the disease phenotypes caused by Dystrophin expression defects in Dmd-E4 mice were successfully repaired by AAV treatment. Wherein, A, RNA in the heart of treated Dmd-E4 mice were performed by reverse transcription PCR, and primers were designed for Exon3 and Exon5 to detect skipping of Exon4 carrying mutations. Dmd is the gene encoding Dystrophin protein in mice, and Gapdh is the internal reference of PCR. B, using method of capillary electrophoresis quantification to determine the ratio of the content of nucleic acid contained in the band with Exon4 skipping to the band without skipping (i.e., included); C, Sanger sequencing was performed on the band with Exon4 skipping, and it was confirmed that Exon4 was completely skipped, and Exon3 and Exon5 were spliced together; D, Western blotting was performed to detect proteins in the heart of treated Dmd-E4 mice. WT mice and untreated mice were used as positive and negative controls, and VCL was the internal reference of large molecular weight. E, Quantitative statistics of bands in Figure D. F, the condition of expression of Dystrophin protein in the heart of Dmd-E4 mice was detected by immunofluorescence staining, including two post-treatment samples. G, the method of small animal heart ultrasound was used to investigate whether the changes in the heart-related physiological structure of Dmd-E4 mice were repaired after AAV treatment. H is the quantification of F, which quantified the proportion of Dystrophin positive expression cells. P-value: $*p < 0.05$, $p < 0.01$, $*p < 0.001$.

As shown in FIG. 4A, RNA in the hearts of treated Dmd-E4 mice was performed reverse transcription PCR, and primers were designed for Exon3 and Exon5 to detect skipping of Exon4 carrying mutations. At the same time, using method of capillary electrophoresis quantification to determine the ratio of the content of nucleic acid contained in the band with Exon4 skipping to the band without skipping (i.e., included). The results are shown in FIG. 4B. Further, Sanger sequencing was performed on the band with Exon4 skipping, and as shown in FIG. 4C, Exon4 was completely skipped, and Exon3 and Exon5 were spliced together. FIG. 3D-F shows that western blotting was performed to detect proteins in the heart of mice, wherein FIG. 4D is the band plot, FIG. 3 panel E is the quantitative statistics of the band in the FIG. 3D. FIG. 4F shows the condition of expression of Dystrophin protein, the results show that the treated Dmd-E4 significantly restored the expression of Dystrophin protein. In addition, the method of small animal heart ultrasound detection was used to investigate whether the changes in the heart-related physiological structure of Dmd-E4 mice were repaired after AAV treatment. Results are shown in FIG. 4G, which shows that the heart-related physiological structure of Dmd-E4 mice was basically repaired after treatment.

Figure 5:
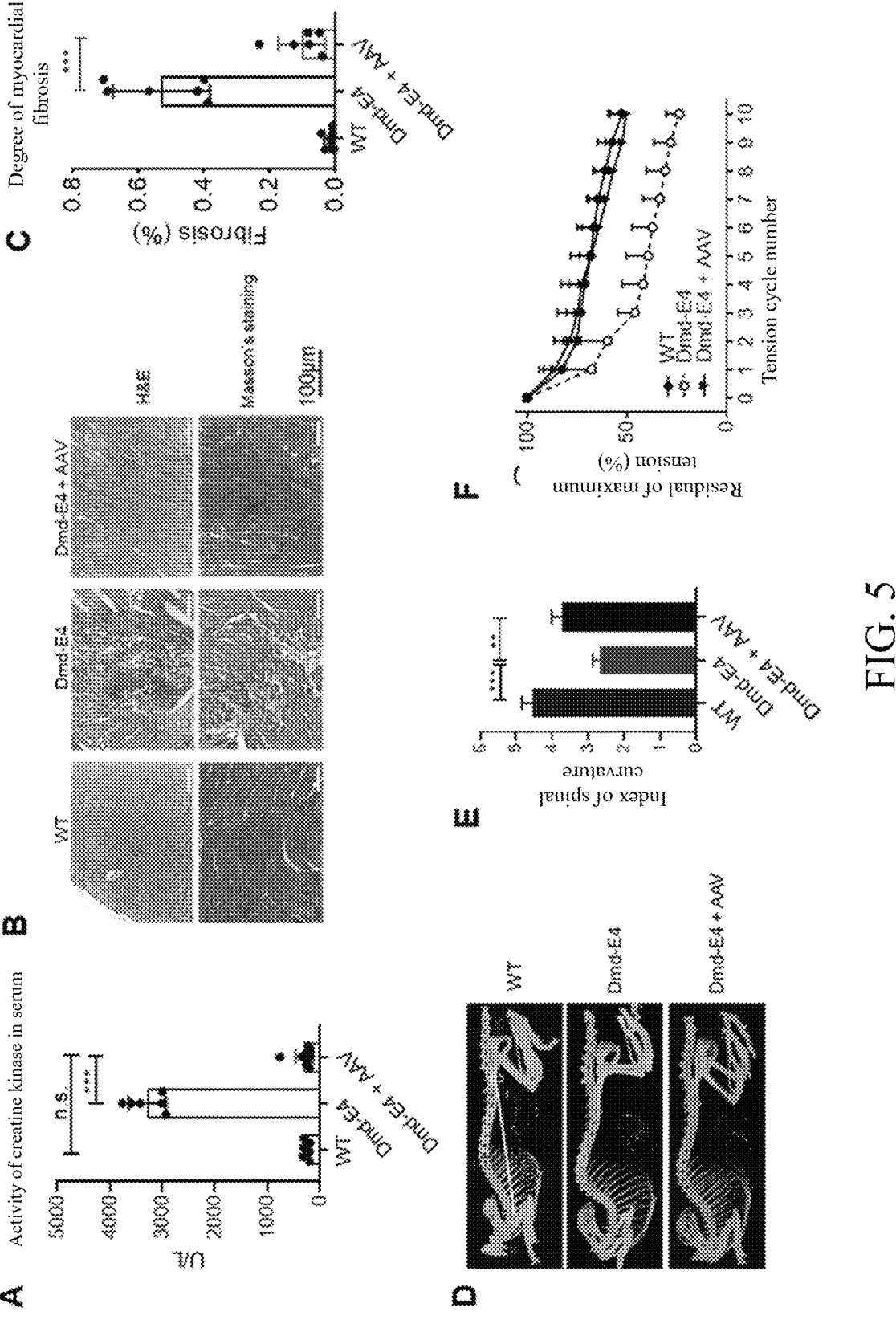
FIG. 5 shows AAV treatment successfully restored muscle function and prolonged survival in Dmd-E4 mice. A, the creatine kinase content in serum of treated Dmd-E4 mice was determined, and WT and untreated Dmd-E4 mice samples were used as controls. B, HE staining and Masson staining were used to evaluate the degree of myocardial inflammatory cell infiltration and fibrosis of Dmd-E4 mice after treatment. C, according to the results of Masson staining, the recovery of myocardial fibrosis in Dmd-E4 mice after treatment was quantitatively counted. D, the method of micro-CT was used to detect the degree of spinal curvature in Dmd-E4 mice, and WT mice and untreated mice samples were used as controls. E, the quantitative statistics of the degree of spinal curvature in Figure D; F, a tension device was used to detect the degradation range of the maximum tension of the whole body muscle of the treated Dmd-E4 mice during the cyclic force process. G, survival statistics of WT mice, and AAV-treated and untreated Dmd-E4 mice; H, the molecular biological evidence of gene editing in cardiomyocytes of Dmd-E4 mice, pre-mRNA of corresponding cells was performed by reverse transcription PCR, and then high-throughput sequencing was performed. It was found that the expected mutation was generated near the location of sgRNA targeting, which is the molecular foundation and basis for the treatment of cardiac disease phenotype in Dmd-E4 mice. $*p < 0.05$, $p < 0.01$, $*p < 0.001$.
Figure 5:
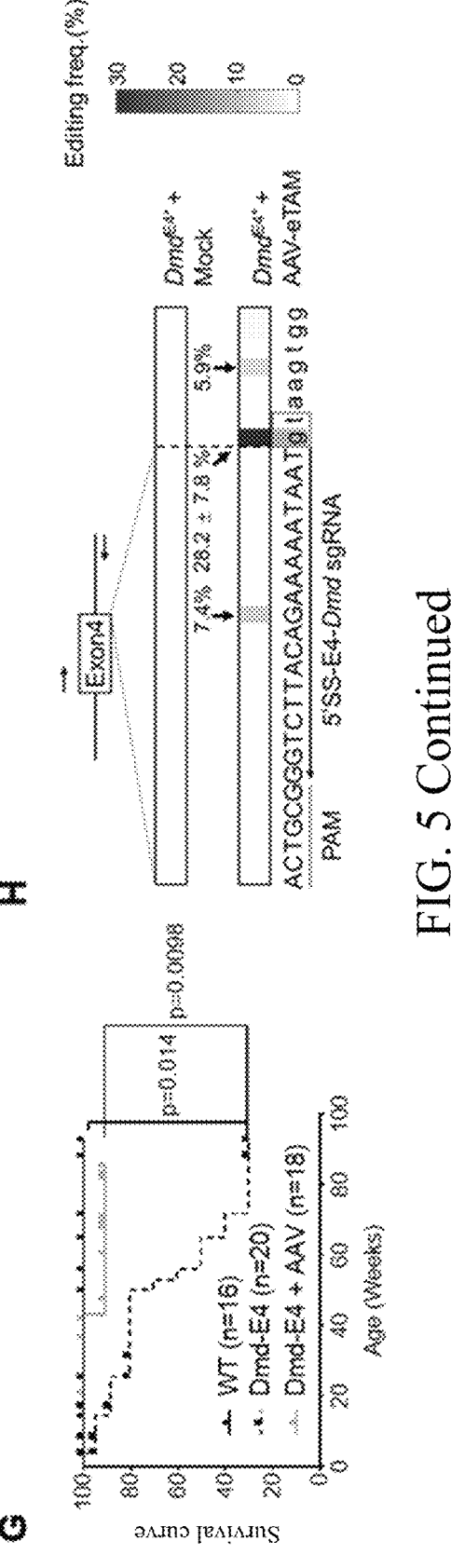

Furthermore, the muscle function and survival of Dmd-E4 mice were verified to recover and prolong or not. FIG. 5A shows the results of the determination of creatine kinase content in the serum of mice, from which it can be seen that the creatine kinase content of treated Dmd-E4 mice was significantly reduced compared to WT and untreated Dmd-E4 mice samples. The method of HE staining and Masson staining was used to evaluate the degree of myocardial inflammatory cell infiltration and fibrosis of Dmd-E4 mice after treatment, and according to the results of Masson staining, the recovery of myocardial fibrosis in treated Dmd-E4 mice was quantitatively counted. As the results shown in FIG. 5B-5C, the degree of myocardial fibrosis of treated Dmd-E4 mice was significantly improved. In addition, the micro-CT method was also used to detect the degree of spinal curvature in Dmd-E4 mice (FIGS. 5D-5E), and a pulling device was used to detect the degradation range of the maximum tension of the whole body muscle of the treated Dmd-E4 mice during the cyclic force process (FIG. 5F). The results show that the the spine curvature of Dmd-E4 mice was relieved after treatment, and the whole body muscle tension of the mice was enhanced, and the survival of Dmd-E4 mice was greatly prolonged (FIG. 5G).

FIG. 5H shows the molecular biological evidence of gene editing in cardiomyocytes of Dmd-E4 mice. The pre-mRNA of the corresponding cells was performed by reverse-transcribed PCR, followed by high-throughput sequencing, and it was found that the expected mutation was generated near the location of the sgRNA targeting, which is the molecular foundation and basis for the treatment of the cardiac disease phenotype of Dmd-E4 mice.

The above results show that the gene editing tool of the present invention can effectively treat and prevent neonatal Dmd-E4 mice.

(B) Gene Therapy in Adult Mice

Grouping: 3-5 homozygous KO Dmd-E4 male mice aged 4-6 weeks were taken as the experimental group to give gene therapy, and 3-5 homozygous KO Dmd-E4 male mice were taken as the control group to give the same amount of PBS.

Administration: About 50 µL of adeno-associated virus (AAV) carrying the gene-editing tool (with a titer of $10^{13}$ v·g·/mL) was administered by tail vein injection or skeletal muscle in situ injection, and control mice were given an equal volume of sterile PBS at the same time;

Sampling and detection: When the mice were treated for about 2 months, in addition to the experimental group and the control group, 3-5 WT male mice of the same age were taken, and the following treatment was carried out at the same time: after anesthetizing the mouse, the function test of the tibial anterior muscle, echocardiogram detection and the like was first performed, and then cardiac arteriovenous blood was collected to sacrifice the mouse. The serum was separated by centrifugation and stored at −80° C., while myocardium, skeletal muscle, tibial anterior muscle, back muscle, liver, brain, kidney and other tissues were collected, and proteins, RNA, genomic DNA of that were extracted. Enough tissue was retained for immunofluorescence staining, hematoxylin eosin staining, etc.

The results show that AAV can be used as a carrier for gene editing tools to achieve efficient gene repair of mutant exons. In the treated Dmd-E4 mice, the pathogenic exon skipping could be observed in the myocardium and multiple muscle tissues, and the expression of Dystrophin protein was restored, and the phenotype of myocardial injury was also significantly repaired, so that adult Dmd-E4 mice were treated.

Figure 6:
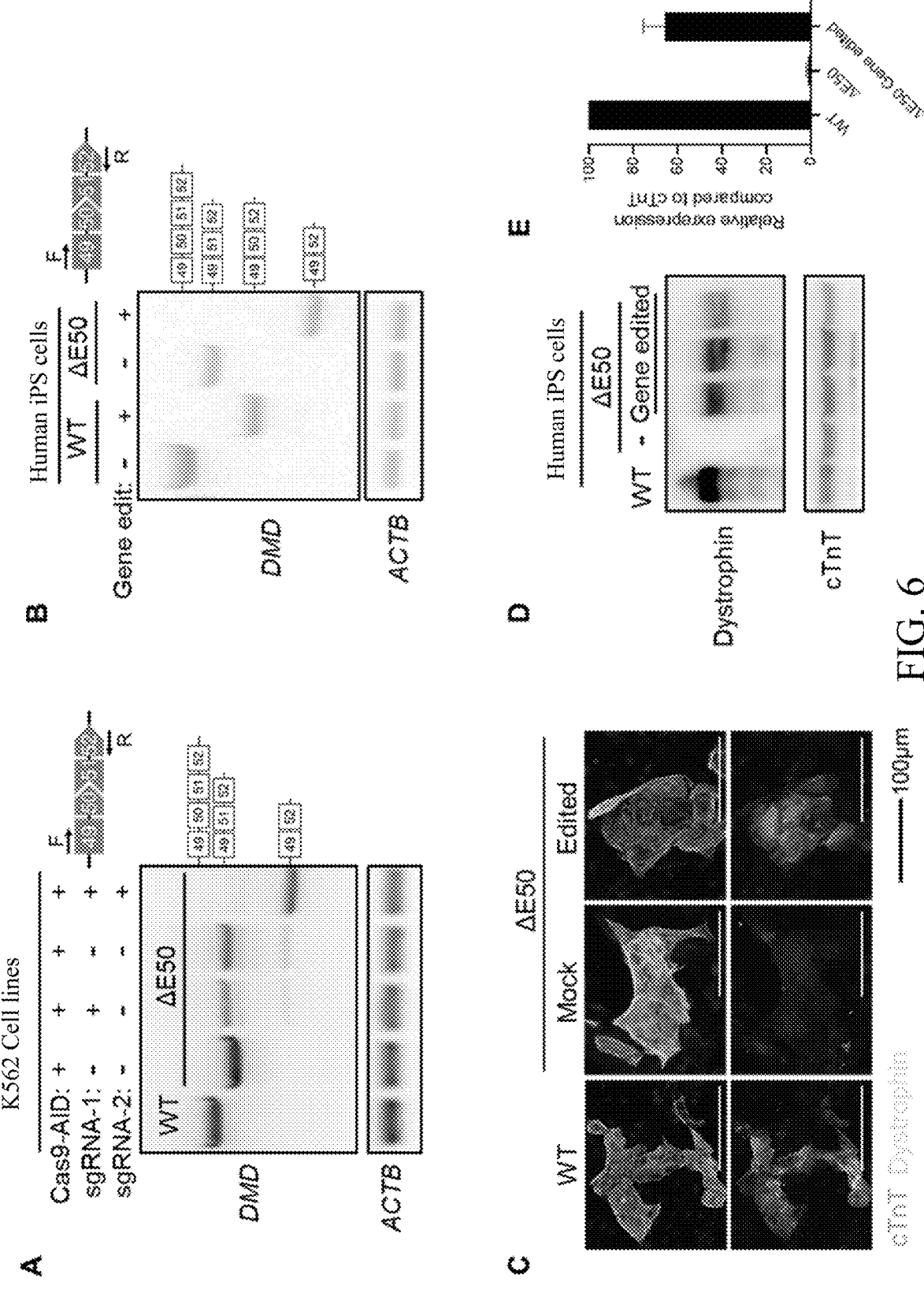
FIG. 6 shows gene editing tools can successfully induce the corresponding modification of DMD genes in human cells. A, two sgRNAs were successfully screened in the K562 cell line, which can induce the skipping of Exon51. The figure shows the results of reverse transcription PCR after RNA extraction in edited K562 cells, indicating that the combination of two sgRNAs can effectively induce Exon50- deficient K562 cells to successfully skip Exon51. B, Exon51 of the DMD gene was induced to be skipped in normal human iPS cells and DMDexon50-deficient cells. C, immunofluorescence detection was used to determine that the expression of Dystrophin protein was restored in the edited iPS cells. D, western blot was used to determine that the expression of Dystrophin was restored in the edited iPS cells. E, the quantitative statistics of protein restored expression in Figure D.

Example 3 Gene Editing of the DMD Model of Human Induced Pluripotent Stem Cells (iPSCs) Successfully Restored the Expression of Dystrophin Protein Gene editing therapy of human cells has also been successfully implemented in the present invention. Firstly, we constructed induced pluripotent stem cells (iPSCs) from normal human peripheral blood mononuclear cells. Then CRISPR-cas9 was used to specifically delete Exon 50 in the Dystrophin coding gene DMD, resulting in a frame shift mutation in the coding sequence of the Dystrophin protein, thereby a mutation type mimicking DMD patients was constructed, which became a good DMD disease model cell. For this cell, we designed the sequence of AID and Cas9 fusion protein and the corresponding sgRNA, and a series of potential regulatory exon splicing elements targeting Exon51 of the DMD gene. The sgRNAs used in this example were sgRNA-12 as shown in SEQ ID NO: 19 and sgRNA-13 as shown in SEQ ID NO: 20, wherein sgRNA-12 mainly targeted exon splicing enhancer as shown in SEQ ID NO: 21 and SEQ ID NO: 22, and sgRNA-13 mainly targeted exon splicing enhancer as shown in SEQ ID NO: 24. The above two sgRNA-12 were screened in human K562 cell lines and could induce the skipping of Exon51. As shown in FIG. 6A, the results of reverse transcription PCR after RNA extraction of edited K562 cells show that both sgRNAs can induce mutations, and the combination of that can effectively induce Exon50-deficient K562 cells to successfully skip Exon51. By inducing the skipping of Exon51, the open reading frame of Dystrophin protein in Exon50-deficient K562 cells can be restored, and the expression of Dystrophin protein can be reconstructed at the same time. The specific implementation plan is as follows:

3.1 Induction of Differentiation of iPS Cells into Cardiomyocytes (1) Human iPS cells cultured on matrix gel were digested with Accutase at 37° C. for 6 min. The reaction was terminated with DMEM medium, and the cells were collected, centrifuged at 1500 rpm for 3 min, and were counted under a microscope.

(2) iPS cells were placed in 12-well plates pre-coated with matrix glue, and the cell density was adjusted to 10,000-20,000 cells/cm². iPS cells were cultured with mTeSR1 medium for 4 days and 10 uM ROCK inhibitor (Y-27632) was added, and the fresh medium was changed every day. ROCK inhibitors are not required when changing the medium.

(3) After 4 days of cell culture, mTeSR1 medium was changed to RPMI/B27-insulin medium containing 6 uM CHIR99021 for 2 days of culture.

(4) CHIR99021 stimulation was removed, and the medium was changed to RPMI/B27-insulin medium for 1 day of culture.

(5) The medium was changed to RPMI/B27-insulin medium containing 5 μm IWR1 for 2 days of culture.

(6) IWR1 stimulation was removed, and the medium was changed to RPMI/B27-insulin medium for 2 days of culture.

The cell culture medium was changed to RPMI/B27 medium, and then the cells were cultured with this medium. The medium was changed every two days to obtain human pluripotent stem cells differentiated into cardiomyocytes.

3.2 Transfection of Gene Editing Tools in Human Pluripotent Stem Cells that Induced Differentiation into Cardiomyocytes (1) On the day before transfection, iPS cells that induced differentiation into cardiomyocytes were digested with Accutase, and were seed in a 6-well plate with 4× 10⁵ cells per well.

(2) After about 24 hours, when the density of iPS cells that induced differentiation into cardiomyocytes reached about 60%, the cell culture medium was changed to antibiotic-free medium.

(3) 2.5 μg plasmids expressing AID and Cas9 mutant fusion protein (e.g., Lenti-V2-AIDx-nSaCas9 (KKH)-Ugi plasmid), 500 ng plasmids expressing UGI (e.g., pCDNA03.1-Ugi) and 1.5 μg sgRNA plasmids were mixed in 150 μl opti-MEM, and 2.5 μl PLUS™ reagent was added and gently mixed.

(4) 12 μl Lipofectamine LTX and 150 μl opti-MEM medium were mixed and added into the plasmids of step (3). They were gently mixed, and incubated at room temperature for 15 min. The reaction product was added into the iPS cells differentiated into cardiomyocytes of step (2);

(5) After 48 h of transfection, 2 μg/ml puromycin was added into the transfected cells. The cells were screened for 3 days and then the drug was withdrawn. After 7 days of transfection, cells were collected for analysis.

3.3 the Detection of the Relevant Indicators of the Edited iPSC (1) The genomic DNA of iPSC before and after editing was extracted to detect whether the corresponding Exon51 mutation occurred.

(2) The iPSC RNA was extracted before and after editing, and reverse transcription PCR was performed to detect whether Exon51 had been skipped at the RNA level. The results are shown in FIG. 6B. Exon51 of the DMD gene was induced to skip in normal human iPS cells and DMD exon50-deficient cells.

(3) The expression of Dystrophin protein was investigated at the protein level of iPSCs before and after editing, and experimental methods included Western Blot, immunofluorescence staining, etc. FIG. 6C shows that immunofluorescence detection was used to determine that the expression of Dystrophin protein was restored in the edited iPS cells. FIG. 6D shows that western blot was used to determine that the expression of Dystrophin was restored in the edited iPS cells. FIG. 6E is the quantitative statistics of protein restored expression in Figure D.

The above results show that in the K562 cell line, a gene editing method that can induce skipping of human DMD gene Exon51 has been successfully constructed, and a series of sequence elements that potentially regulate exon skipping have been identified. This gene editing scheme can be further used to successfully carry out therapeutic modification of DMD disease model cells iPSC and restore the expression of Dystrophin protein.

In addition, the corresponding exon splicing enhancer of the present invention such as SEQ ID NO: 21-SEQ ID NO: 24 are all targeted by the rest of the sgRNA-1-sgRNA-11 as shown in SEQ ID NO: 7-SEQ ID NO: 18. When it is constructed into a gene editing tool, it can efficiently induce skipping of Exon51, thereby realizing the treatment of human DMD.

Obviously, the above embodiments are only examples for clarity, and do not qualify the embodiment. For those of ordinary skill in the art, other different forms of change or variation can be made on the basis of the above description. It is unnecessary and impossible to enumerate all embodiments here. The obvious change or variation derived therefrom remains within the scope of protection of the present invention.

The invention claimed is:

1. A Duchenne muscular dystrophy-related gene editing tool, comprising a fusion protein of a cytosine deaminase and Cas9 mutant, a single stranded guide RNA (sgRNA) targeting the human DMD gene Exon51 with the nucleotide sequence as shown in SEQ ID NO. 20 and a vector;

wherein the cytosine deaminase is AID, and the amino acid sequence of the fusion protein of AID and Cas9 mutant is as shown in SEQ ID NO. 1.

2. The gene editing tool of claim 1, wherein the gene editing tool is packaged by an adeno-associated viral (AAV) vector.

3. The gene editing tool of claim 2, wherein the promoter of the adeno-associated viral (AAV) vector is Syn100 promoter or a promoter based on ck8a, mhck7.

4. The gene editing tool of claim 2, wherein the nucleotide sequence of the adeno-associated viral (AAV) vector is shown in SEQ ID NO: 3.

5. A method for treating Duchenne muscular dystrophy which comprises administering the gene editing tool comprising the sgRNA of claim 1 to a subject in need.

6. The gene editing tool of claim 1, comprising a fusion protein of a cytosine deaminase and Cas9 mutant, a sgRNA composition and a vector;

wherein the sgRNA composition comprises sgRNA-13 targeting the human DMD gene Exon51 with the nucleotide sequence as shown in SEQ ID NO: 20 and sgRNA-12 targeting the human DMD gene Exon51 with the nucleotide sequence as shown in SEQ ID NO: 19;

the vector comprises nucleic acid sequences expressing the fusion protein and the sgRNA composition;

the cytosine deaminase is AID, and the amino acid sequence of the fusion protein of AID and Cas9 mutant is as shown in SEQ ID NO: 1.

7. The gene editing tool of claim 1, wherein the nucleic acid sequence of the fusion protein of AID and Cas9 mutant is as shown in SEQ ID NO: 2.

8. A method for treating Duchenne muscular dystrophy which comprises administering the gene editing tool of claim 6 to a subject in need thereof.

* * * * *

SEQUENCE LISTING

<160> NUMBER OF SEQ ID NOS: 24

<210> SEQ ID NO 1
<211> LENGTH: 1420
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of fusion protein of
      AID-Cas9 mutant

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Met Asp Ser Leu Leu Met Asn Arg
        35                  40                  45

Arg Glu Phe Leu Tyr Gln Phe Lys Asn Val Arg Trp Ala Lys Gly Arg
    50                  55                  60

Arg Glu Thr Tyr Leu Cys Tyr Val Val Lys Arg Arg Asp Ser Ala Thr
65                  70                  75                  80

Ser Phe Ser Leu Asp Phe Gly Tyr Leu Arg Asn Lys Asn Gly Cys His
                85                  90                  95

Val Glu Leu Leu Phe Leu Arg Tyr Ile Ser Asp Trp Asp Leu Asp Pro
            100                 105                 110

Gly Arg Cys Tyr Arg Val Thr Trp Phe Ile Ser Trp Ser Pro Cys Tyr
            115                 120                 125

Asp Cys Ala Arg His Val Ala Asp Phe Leu Arg Gly Asn Pro Asn Leu
            130                 135                 140

Ser Leu Arg Ile Phe Thr Ala Arg Leu Tyr Phe Cys Glu Asp Arg Lys
145                 150                 155                 160

Ala Glu Pro Glu Gly Leu Arg Arg Leu His Arg Ala Gly Val Gln Ile
                165                 170                 175

Ala Ile Met Thr Phe Lys Asp Tyr Phe Tyr Cys Trp Asn Thr Phe Val
                180                 185                 190

Glu Asn His Gly Arg Thr Phe Lys Ala Trp Glu Gly Leu His Glu Asn
            195                 200                 205

Ser Val Arg Leu Ser Arg Gln Leu Arg Arg Ile Leu Leu Pro Ser Gly
    210                 215                 220

Ser Glu Thr Pro Gly Thr Ser Glu Ser Ala Thr Pro Glu Ser Gly Lys
225                 230                 235                 240

Arg Asn Tyr Ile Leu Gly Leu Ala Ile Gly Ile Thr Ser Val Gly Tyr
                245                 250                 255

Gly Ile Ile Asp Tyr Glu Thr Arg Asp Val Ile Asp Ala Gly Val Arg
                260                 265                 270

Leu Phe Lys Glu Ala Asn Val Glu Asn Asn Glu Gly Arg Arg Ser Lys
            275                 280                 285

Arg Gly Ala Arg Arg Leu Lys Arg Arg Arg His Arg Ile Gln Arg
    290                 295                 300

Val Lys Lys Leu Leu Phe Asp Tyr Asn Leu Leu Thr Asp His Ser Glu
305                 310                 315                 320

Leu Ser Gly Ile Asn Pro Tyr Glu Ala Arg Val Lys Gly Leu Ser Gln
            325                 330                 335

-continued

```
Lys Leu Ser Glu Glu Glu Phe Ser Ala Ala Leu Leu His Leu Ala Lys
            340                 345                 350

Arg Arg Gly Val His Asn Val Asn Glu Val Glu Glu Asp Thr Gly Asn
            355                 360                 365

Glu Leu Ser Thr Lys Glu Gln Ile Ser Arg Asn Ser Lys Ala Leu Glu
    370                 375                 380

Glu Lys Tyr Val Ala Glu Leu Gln Leu Glu Arg Leu Lys Lys Asp Gly
385                 390                 395                 400

Glu Val Arg Gly Ser Ile Asn Arg Phe Lys Thr Ser Asp Tyr Val Lys
                405                 410                 415

Glu Ala Lys Gln Leu Leu Lys Val Gln Lys Ala Tyr His Gln Leu Asp
            420                 425                 430

Gln Ser Phe Ile Asp Thr Tyr Ile Asp Leu Leu Glu Thr Arg Arg Thr
            435                 440                 445

Tyr Tyr Glu Gly Pro Gly Glu Gly Ser Pro Phe Gly Trp Lys Asp Ile
    450                 455                 460

Lys Glu Trp Tyr Glu Met Leu Met Gly His Cys Thr Tyr Phe Pro Glu
465                 470                 475                 480

Glu Leu Arg Ser Val Lys Tyr Ala Tyr Asn Ala Asp Leu Tyr Asn Ala
                485                 490                 495

Leu Asn Asp Leu Asn Asn Leu Val Ile Thr Arg Asp Glu Asn Glu Lys
            500                 505                 510

Leu Glu Tyr Tyr Glu Lys Phe Gln Ile Ile Glu Asn Val Phe Lys Gln
            515                 520                 525

Lys Lys Lys Pro Thr Leu Lys Gln Ile Ala Lys Glu Ile Leu Val Asn
    530                 535                 540

Glu Glu Asp Ile Lys Gly Tyr Arg Val Thr Ser Thr Gly Lys Pro Glu
545                 550                 555                 560

Phe Thr Asn Leu Lys Val Tyr His Asp Ile Lys Asp Ile Thr Ala Arg
                565                 570                 575

Lys Glu Ile Ile Glu Asn Ala Glu Leu Leu Asp Gln Ile Ala Lys Ile
            580                 585                 590

Leu Thr Ile Tyr Gln Ser Ser Glu Asp Ile Gln Glu Glu Leu Thr Asn
            595                 600                 605

Leu Asn Ser Glu Leu Thr Gln Glu Glu Ile Glu Gln Ile Ser Asn Leu
    610                 615                 620

Lys Gly Tyr Thr Gly Thr His Asn Leu Ser Leu Lys Ala Ile Asn Leu
625                 630                 635                 640

Ile Leu Asp Glu Leu Trp His Thr Asn Asp Asn Gln Ile Ala Ile Phe
                645                 650                 655

Asn Arg Leu Lys Leu Val Pro Lys Lys Val Asp Leu Ser Gln Gln Lys
            660                 665                 670

Glu Ile Pro Thr Thr Leu Val Asp Asp Phe Ile Leu Ser Pro Val Val
            675                 680                 685

Lys Arg Ser Phe Ile Gln Ser Ile Lys Val Ile Asn Ala Ile Ile Lys
    690                 695                 700

Lys Tyr Gly Leu Pro Asn Asp Ile Ile Ile Glu Leu Ala Arg Glu Lys
705                 710                 715                 720

Asn Ser Lys Asp Ala Gln Lys Met Ile Asn Glu Met Gln Lys Arg Asn
                725                 730                 735

Arg Gln Thr Asn Glu Arg Ile Glu Glu Ile Ile Arg Thr Thr Gly Lys
            740                 745                 750

Glu Asn Ala Lys Tyr Leu Ile Glu Lys Ile Lys Leu His Asp Met Gln
```

-continued

```
              755                 760                 765
Glu Gly Lys Cys Leu Tyr Ser Leu Glu Ala Ile Pro Leu Glu Asp Leu
        770                 775                 780
Leu Asn Asn Pro Phe Asn Tyr Glu Val Asp His Ile Ile Pro Arg Ser
785                 790                 795                 800
Val Ser Phe Asp Asn Ser Phe Asn Asn Lys Val Leu Val Lys Gln Glu
                805                 810                 815
Glu Asn Ser Lys Lys Gly Asn Arg Thr Pro Phe Gln Tyr Leu Ser Ser
                820                 825                 830
Ser Asp Ser Lys Ile Ser Tyr Glu Thr Phe Lys Lys His Ile Leu Asn
                835                 840                 845
Leu Ala Lys Gly Lys Gly Arg Ile Ser Lys Thr Lys Lys Glu Tyr Leu
        850                 855                 860
Leu Glu Glu Arg Asp Ile Asn Arg Phe Ser Val Gln Lys Asp Phe Ile
865                 870                 875                 880
Asn Arg Asn Leu Val Asp Thr Arg Tyr Ala Thr Arg Gly Leu Met Asn
                885                 890                 895
Leu Leu Arg Ser Tyr Phe Arg Val Asn Asn Leu Asp Val Lys Val Lys
            900                 905                 910
Ser Ile Asn Gly Gly Phe Thr Ser Phe Leu Arg Arg Lys Trp Lys Phe
            915                 920                 925
Lys Lys Glu Arg Asn Lys Gly Tyr Lys His His Ala Glu Asp Ala Leu
        930                 935                 940
Ile Ile Ala Asn Ala Asp Phe Ile Phe Lys Glu Trp Lys Lys Leu Asp
945                 950                 955                 960
Lys Ala Lys Lys Val Met Glu Asn Gln Met Phe Glu Glu Lys Gln Ala
                965                 970                 975
Glu Ser Met Pro Glu Ile Glu Thr Glu Gln Glu Tyr Lys Glu Ile Phe
            980                 985                 990
Ile Thr Pro His Gln Ile Lys His  Ile Lys Asp Phe Lys  Asp Tyr Lys
            995                 1000                1005
Tyr Ser  His Arg Val Asp Lys  Lys Pro Asn Arg Lys  Leu Ile Asn
        1010                1015                1020
Asp Thr  Leu Tyr Ser Thr Arg  Lys Asp Asp Lys Gly  Asn Thr Leu
        1025                1030                1035
Ile Val  Asn Asn Leu Asn Gly  Leu Tyr Asp Lys Asp  Asn Asp Lys
        1040                1045                1050
Leu Lys  Lys Leu Ile Asn Lys  Ser Pro Glu Lys Leu  Leu Met Tyr
        1055                1060                1065
His His  Asp Pro Gln Thr Tyr  Gln Lys Leu Lys Leu  Ile Met Glu
        1070                1075                1080
Gln Tyr  Gly Asp Glu Lys Asn  Pro Leu Tyr Lys Tyr  Tyr Glu Glu
        1085                1090                1095
Thr Gly  Asn Tyr Leu Thr Lys  Tyr Ser Lys Lys Asp  Asn Gly Pro
        1100                1105                1110
Val Ile  Lys Lys Ile Lys Tyr  Tyr Gly Asn Lys Leu  Asn Ala His
        1115                1120                1125
Leu Asp  Ile Thr Asp Asp Tyr  Pro Asn Ser Arg Asn  Lys Val Val
        1130                1135                1140
Lys Leu  Ser Leu Lys Pro Tyr  Arg Phe Asp Val Tyr  Leu Asp Asn
        1145                1150                1155
Gly Val  Tyr Lys Phe Val Thr  Val Lys Asn Leu Asp  Val Ile Lys
        1160                1165                1170
```

-continued

```
Lys Glu Asn Tyr Tyr Glu Val Asn Ser Lys Cys Tyr Glu Glu Ala
    1175            1180            1185

Lys Lys Leu Lys Lys Ile Ser Asn Gln Ala Glu Phe Ile Ala Ser
    1190            1195            1200

Phe Tyr Lys Asn Asp Leu Ile Lys Ile Asn Gly Glu Leu Tyr Arg
    1205            1210            1215

Val Ile Gly Val Asn Asn Asp Leu Leu Asn Arg Ile Glu Val Asn
    1220            1225            1230

Met Ile Asp Ile Thr Tyr Arg Glu Tyr Leu Glu Asn Met Asn Asp
    1235            1240            1245

Lys Arg Pro Pro His Ile Ile Lys Thr Ile Ala Ser Lys Thr Gln
    1250            1255            1260

Ser Ile Lys Lys Tyr Ser Thr Asp Ile Leu Gly Asn Leu Tyr Glu
    1265            1270            1275

Val Lys Ser Lys Lys His Pro Gln Ile Ile Lys Lys Gly Gly Ser
    1280            1285            1290

Ser Gly Gly Ser Thr Asn Leu Ser Asp Ile Ile Glu Lys Glu Thr
    1295            1300            1305

Gly Lys Gln Leu Val Ile Gln Glu Ser Ile Leu Met Leu Pro Glu
    1310            1315            1320

Glu Val Glu Glu Val Ile Gly Asn Lys Pro Glu Ser Asp Ile Leu
    1325            1330            1335

Val His Thr Ala Tyr Asp Glu Ser Thr Asp Glu Asn Val Met Leu
    1340            1345            1350

Leu Thr Ser Asp Ala Pro Glu Tyr Lys Pro Trp Ala Leu Val Ile
    1355            1360            1365

Gln Asp Ser Asn Gly Glu Asn Lys Ile Lys Met Leu Ser Gly Gly
    1370            1375            1380

Ser Pro Lys Lys Lys Arg Lys Val Gly Ser Tyr Pro Tyr Asp Val
    1385            1390            1395

Pro Asp Tyr Ala Tyr Pro Tyr Asp Val Pro Asp Tyr Ala Tyr Pro
    1400            1405            1410

Tyr Asp Val Pro Asp Tyr Ala
    1415            1420
```

```
<210> SEQ ID NO 2
<211> LENGTH: 4263
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleotide sequence of fusion protein of
     AID-Cas9 mutant

<400> SEQUENCE: 2
atggactata aggaccacga cggagactac aaggatcatg atattgatta caaagacgat      60
gacgataaga tggccccaaa gaagaagcgg aaggtcggta ccacggagt cccagcagcc      120 atggacagcc tcttgatgaa ccggagggag tttctttacc aattcaaaaa tgtccgctgg      180
gctaagggtc ggcgtgagac ctacctgtgc tacgtagtga agaggcgtga cagtgctaca      240
tccttttcac tggactttgg ttatcttcgc aataagaacg ctgccacgt ggaattgctc      300 ttcctccgct acatctcgga ctgggaccta gaccctggcc gctgctaccg cgtcacctgg      360
ttcatctcct ggagcccctg ctacgactgt gcccgacatg tggccgactt ctgcgaggg      420
```

-continued

```
aaccccaacc tcagtctgag gatcttcacc gcgcgcctct acttctgtga ggaccgcaag    480
gctgagcccg aggggctgcg gcggctgcac cgcgccgggg tgcaaatagc catcatgacc    540
ttcaaagatt atttttactg ctggaatact tttgtagaaa accatggaag aactttcaaa    600
gcctgggaag ggctgcatga aaattcagtt cgtctatcca gacagcttcg gcgcatcctt    660
ttgcccagcg gcagcgagac tcccgggacc tcagagtccg ccacacccga aagcggcaag    720
aggaactaca tcctgggcct ggccatcggc atcaccagcg tgggctacgg catcatcgac    780
tacgagacca gggacgtgat cgacgccggc gtgaggctgt tcaaggaggc caacgtggag    840
aacaacgagg gcaggaggag caagaggggc gccaggaggc tgaagaggag gaggaggcac    900
aggatccaga gggtgaagaa gctgctgttc gactacaacc tgctgaccga ccacagcgag    960
ctgagcggca tcaacccctta cgaggccagg gtgaagggcc tgagccagaa gctgagcgag   1020
gaggagttca gcgccgccct gctgcacctg gccaagagga ggggcgtgca caacgtgaac   1080
gaggtggagg aggacaccgg caacgagctg agcaccaagg agcagatcag caggaacagc   1140
aaggccctgg aggagaagta cgtggccgag ctgcagctgg agaggctgaa gaaggacggc   1200
gaggtgaggg gcagcatcaa caggttcaag accagcgact acgtgaagga ggccaagcag   1260
ctgctgaagg tgcagaaggc ctaccaccag ctggaccaga gcttcatcga cacctacatc   1320
gacctgctgg agaccaggag gacctactac gagggccctg gcgagggcag ccctttcggc   1380
tggaaggaca tcaaggagtg gtacgagatg ctgatgggcc actgcaccta cttccctgag   1440
gagctgagga gcgtgaagta cgcctacaac gccgacctgt acaacgccct gaacgacctg   1500
aacaacctgg tgatcaccag ggacgagaac gagaagctgg agtactacga gaagttccag   1560
atcatcgaga acgtgttcaa gcagaagaag aagcctaccc tgaagcagat cgccaaggag   1620
atcctggtga acgaggagga catcaagggc tacagggtga ccagcaccgg caagcctgag   1680
ttcaccaacc tgaaggtgta ccacgacatc aaggacatca ccgccaggaa ggagatcatc   1740
gagaacgccg agctgctgga ccagatcgcc aagatcctga ccatctacca gagcagcgag   1800
gacatccagg aggagctgac caacctgaac agcgagctga cccaggagga gatcgagcag   1860
atcagcaacc tgaagggcta caccggcacc cacaacctga gcctgaaggc catcaacctg   1920
atcctggacg agctgtggca caccaacgac aaccagatcg ccatcttcaa caggctgaag   1980
ctggtgccta gaaggtgga cctgagccag cagaaggaga tccctaccac cctggtggac   2040
gacttcatcc tgagccctgt ggtgaagagg agcttcatcc agagcatcaa ggtgatcaac   2100
gccatcatca gaagtacgg cctgcctaac gacatcatca tcgagctggc cagggagaag   2160
aacagcaagg acgcccagaa gatgatcaac gagatgcaga gaggaacag gcagaccaac   2220 gagaggatca aggagatcat caggaccacc ggcaaggaga cgccaagta cctgatcgag   2280 aagatcaagc tgcacgacat gcaggagggc aagtgcctgt acagcctgga ggccatccct   2340
ctggaggacc tgctgaacaa ccctttcaac tacgaggtgg accacatcat ccctaggagc   2400
gtgagcttcg acaacagctt caacaacaag gtgctggtga gcaggagga gaacagcaag   2460 aagggcaaca ggacccctt ccagtacctg agcagcagcg acagcaagat cagctacgag   2520
accttcaaga agcacatcct gaacctggcc aagggcaagg gcaggatcag caagaccaag   2580
aaggagtacc tgctggagga gaggacatc aacaggttca gcgtgcagaa ggacttcatc   2640
aacaggaacc tggtggacac caggtacgcc accagggggcc tgatgaacct gctgaggagc   2700
tacttcaggg tgaacaacct ggacgtgaag gtgaagagca tcaacggcgg cttcaccagc   2760
```

-continued

```
ttcctgagga ggaagtggaa gttcaagaag gagaggaaca agggctacaa gcaccacgcc       2820
gaggacgccc tgatcatcgc caacgccgac ttcatcttca aggagtggaa gaagctggac       2880
aaggccaaga aggtgatgga gaaccagatg ttcgaggaga agcaggccga gagcatgcct       2940
gagatcgaga ccgagcagga gtacaaggag atcttcatca cccctcacca gatcaagcac       3000
atcaaggact tcaaggacta caagtacagc cacagggtgg acaagaagcc taacaggaag       3060
ctgatcaacg acaccctgta cagcaccagg aaggacgaca agggcaacac cctgatcgtg       3120
aacaacctga acggcctgta cgacaaggac aacgacaagc tgaagaagct gatcaacaag       3180
agccctgaga agctgctgat gtaccaccac gaccctcaga cctaccagaa gctgaagctg       3240
atcatggagc agtacggcga cgagaagaac cctctgtaca gtactacga ggagaccggc        3300 aactacctga ccaagtacag caagaaggac aacggccctg tgatcaagaa gatcaagtac       3360
tacggcaaca agctgaacgc ccacctggac atcaccgacg actaccctaa cagcaggaac       3420
aaggtggtga gctgagcct gaagccttac aggttcgacg tgtacctgga caacggcgtg        3480
tacaagttcg tgaccgtgaa gaacctggac gtgatcaaga aggagaacta ctacgaggtg       3540
aacagcaagt gctacgagga ggccaagaag ctgaagaaga tcagcaacca ggccgagttc       3600
atcgccagct tctacaagaa cgacctgatc aagatcaacg gcgagctgta cagggtgatc       3660
ggcgtgaaca cgacctgct gaacaggatc gaggtgaaca tgatcgacat cacctacagg        3720
gagtacctgg agaacatgaa cgacaagagg cctcctcaca tcatcaagac catcgccagc       3780
aagacccaga gcatcaagaa gtacagcacc gacatcctgg caacctgta cgaggtgaag        3840 agcaagaagc accctcagat catcaagaag ggcggcagca cggcggcag caccaacctg        3900 agcgacatca tcgagaagga gaccggtaag caactggtta tccaggaatc catcctcatg       3960
ctcccagagg aggtggaaga agtcattggg aacaagccgg aaagcgatat actcgtgcac       4020
accgcctacg acgagagcac cgacgagaat gtcatgcttc tgactagcga cgccctgaa        4080 tacaagcctt gggctctggt catacaggat agcaacggtg agaacaagat taagatgctc       4140
tctggtggtt ctcccaagaa gaagaggaaa gtcggatcct acccatacga tgttccagat       4200
tacgcttacc catacgatgt tccagattac gcttacccat acgatgttcc agattacgct       4260
taa                                                                      4263
```

<210> SEQ ID NO 3
<211> LENGTH: 7661
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Sequence of AAV plasmid vector expressing
     fusion protein of AID-Cas9 mutant

<400> SEQUENCE: 3

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gactcgacg gccgtccgcc ctcggcacca ttcctcacga        180
caccgaaata tggcgacggg tgaggaatgg tggggagtta tttttagagc ggtgaggaat       240
ggtgggcagg cagcaggtgt tggggggagtt attttttagag cggggagtta tttttagagc     300
ggtgaggaat ggtggacacc gaaatatggc gacgggtgag gaatggtgcc gtcgccatat       360
ttgggtgtcc cgtccgccct cggccggggc cgcattcctg ggggccgggc ggtgctcccg       420
```

```
cccgcctcga taaaaggctc cggggccggc ggcggcccac gagctacccg gaggagcggg      480
aggcgtctct gccagcggtc cgacgcgcag tcagcaccag gtaggtgggc accgcgccgt      540
gccgtgccgc tagctaatac gactcactat agggagagcc gccaccatgg actataagga      600
ccacgacgga gactacaagg atcatgatat tgattacaaa gacgatgacg ataagatggc      660
cccaaagaag aagcggaagg tcggtatcca cggagtccca gcagccatgg acagcctctt      720
gatgaaccgg agggagtttc tttaccaatt caaaaatgtc cgctgggcta agggtcggcg      780
tgagacctac ctgtgctacg tagtgaagag gcgtgacagt gctacatcct tttcactgga      840
ctttggttat cttcgcaata agaacggctg ccacgtggaa ttgctcttcc tccgctacat      900
ctcggactgg gacctagacc ctggccgctg ctaccgcgtc acctggttca tctcctggag      960
cccctgctac gactgtgccc gacatgtggc cgactttctg cgagggaacc ccaacctcag     1020
tctgaggatc ttcaccgcgc gcctctactt ctgtgaggac cgcaaggctg agcccgaggg     1080
gctgcggcgg ctgcaccgcg ccggggtgca aatagccatc atgaccttca agattatt      1140 ttactgctgg aatacttttg tagaaaacca tggaagaact ttcaaagcct gggaagggct     1200
gcatgaaaat tcagttcgtc tatccagaca gcttcggcgc atccttttgc ccagcggcag     1260
cgagactccc gggacctcag agtccgccac acccgaaagc ggcaagagga actacatcct     1320
gggcctggcc atcggcatca ccagcgtggg ctacggcatc atcgactacg agaccaggga     1380
cgtgatcgac gccggcgtga ggctgttcaa ggaggccaac gtggagaaca cgagggcag     1440 gaggagcaag aggggcgcca ggaggctgaa gaggaggagg aggcacagga tccagagggt     1500
gaagaagctg ctgttcgact acaacctgct gaccgaccac agcgagctga gcggcatcaa     1560
cccttacgag gccagggtga agggcctgag ccagaagctg agcgaggagg agttcagcgc     1620
cgccctgctg cacctggcca agaggagggg cgtgcacaac gtgaacgagg tggaggagga     1680
caccggcaac gagctgagca ccaaggagca gatcagcagg aacagcaagg ccctggagga     1740
gaagtacgtg gccgagctgc agctggagag gctgaagaag acggcgagg tgaggggcag     1800 catcaacagg ttcaagacca gcgactacgt gaaggaggcc aagcagctgc tgaaggtgca     1860
gaaggcctac caccagctgg accagagctt catcgacacc tacatcgacc tgctggagac     1920
caggaggacc tactacgagg gccctggcga gggcagccct ttcggctgga aggacatcaa     1980
ggagtggtac gagatgctga tgggccactg cacctacttc cctgaggagc tgaggagcgt     2040
gaagtacgcc tacaacgccg acctgtacaa cgccctgaac gacctgaaca acctggtgat     2100
caccagggac gagaacgaga gctggagta ctacgagaag ttccagatca tcgagaacgt     2160
gttcaagcag aagaagaagc ctaccctgaa gcagatcgcc aaggagatcc tggtgaacga     2220
ggaggacatc aagggctaca gggtgaccag caccggcaag cctgagttca ccaacctgaa     2280
ggtgtaccac gacatcaagg acatcaccgc caggaaggag atcatcgaga cgccgagct     2340 gctggaccag atcgccaaga tcctgaccat ctaccagagc agcgaggaca tccaggagga     2400
gctgaccaac ctgaacagcg agctgaccca ggaggagatc gagcagatca gcaacctgaa     2460
gggctacacc ggcacccaca acctgagcct gaaggccatc aacctgatcc tggacgagct     2520
gtggcacacc aacgacaacc agatcgccat cttcaacagg ctgaagctgg tgcctaagaa     2580
ggtggacctg agccagcaga aggagatccc taccaccctg gtggacgact tcatcctgag     2640
ccctgtggtg aagaggagct tcatccagag catcaaggtg atcaacgcca tcatcaagaa     2700
gtacggcctg cctaacgaca tcatcatcga gctggccagg gagaagaaca gcaaggacgc     2760
```

-continued

```
ccagaagatg atcaacgaga tgcagaagag gaacaggcag accaacgaga ggatcgagga    2820
gatcatcagg accaccggca aggagaacgc caagtacctg atcgagaaga tcaagctgca    2880
cgacatgcag gagggcaagt gcctgtacag cctggaggcc atccctctgg aggacctgct    2940
gaacaaccct ttcaactacg aggtggacca catcatccct aggagcgtga gcttcgacaa    3000
cagcttcaac aacaaggtgc tggtgaagca ggaggagaac agcaagaagg gcaacaggac    3060 cccttttccag tacctgagca gcagcgacac caagatcagc tacgagacct tcaagaagca    3120
catcctgaac ctggccaagg gcaagggcag gatcagcaag accaagaagg agtacctgct    3180
ggaggagagg gacatcaaca ggttcagcgt gcagaaggac ttcatcaaca ggaacctggt    3240
ggacaccagg tacgccacca ggggcctgat gaacctgctg aggagctact tcagggtgaa    3300
caacctggac gtgaaggtga agagcatcaa cggcggcttc accagcttcc tgaggaggaa    3360
gtggaagttc aagaaggaga ggaacaaggg ctacaagcac cacgccgagg acgccctgat    3420
catcgccaac gccgacttca tcttcaagga gtggaagaag ctggacaagg ccaagaaggt    3480
gatggagaac cagatgttcg aggagaagca ggccgagagc atgcctgaga tcgagaccga    3540
gcaggagtac aaggagatct tcatcacccc tcaccagatc aagcacatca aggacttcaa    3600
ggactacaag tacagccaca gggtggacaa gaagcctaac aggaagctga tcaacgacac    3660
cctgtacagc accaggaagg acgacaaggg caacacccctg atcgtgaaca acctgaacgg    3720
cctgtacgac aaggacaacg acaagctgaa gaagctgatc aacaagagcc ctgagaagct    3780
gctgatgtac caccacgacc ctcagaccta ccagaagctg aagctgatca tggagcagta    3840
cggcgacgag aagaaccctc tgtacaagta ctacgaggag accggcaact acctgaccaa    3900
gtacagcaag aaggacaacg gccctgtgat caagaagatc aagtactacg gcaacaagct    3960
gaacgcccac ctggacatca ccgacgacta ccctaacagc aggaacaagg tggtgaagct    4020
gagcctgaag ccttacaggt tcgacgtgta cctggacaac ggcgtgtaca agttcgtgac    4080
cgtgaagaac ctgacgtga tcaagaagga gaactactac gaggtgaaca gcaagtgcta    4140
cgaggaggcc aagaagctga agaagatcag caaccaggcc gagttcatcg ccagcttcta    4200
caagaacgac ctgatcaaga tcaacggcga gctgtacagg gtgatcggcg tgaacaacga    4260
cctgctgaac aggatcgagg tgaacatgat cgacatcacc tacagggagt acctggagaa    4320
catgaacgac aagaggcctc ctcacatcat caagaccatc gccagcaaga cccagagcat    4380
caagaagtac agcaccgaca tcctgggcaa cctgtacgag gtgaagagca gaaagcaccc    4440
tcagatcatc aagaagggcg gcagcagcgg cggcagcacc aacctgagcg acatcatcga    4500
gaaggagacc ggtaagcaac tggttatcca ggaatccatc ctcatgctcc agaggaggt    4560 ggaagaagtc attgggaaca agccggaaag cgatatactc gtgcacaccg cctacgacga    4620
gagcaccgac gagaatgtca tgcttctgac tagcgacgcc cctgaataca agccttgggc    4680
tctggtcata caggatagca acggtgagaa caagattaag atgctctctg gtggttctcc    4740
caagaagaag aggaaagtcg gatcctaccc atacgatgtt ccagattacg cttacccata    4800
cgatgttcca gattacgctt acccatacga tgttccagat tacgcttaag aattctagca    4860
ataaaggatc gtttattttc attggaagcg tgtgttggtt ttttgatcag gcgcggcggc    4920
cgcaggaacc cctagtgatg gagttggcca ctccctctct gcgcgctcgc tcgctcactg    4980
aggccgggcg accaaaggtc gcccgacgcc cgggctttgc ccgggcggcc tcagtgagcg    5040
agcgagcgcg cagctgcctg caggggcgcc tgatgcggta ttttctcctt acgcatctgt    5100
gcggtatttc acaccgcata cgtcaaagca accatagtac gcgccctgta gcggcgcatt    5160
```

-continued

```
aagcgcggcg ggtgtggtgg ttacgcgcag cgtgaccgct acacttgcca gcgccttagc     5220
gcccgctcct ttcgctttct tcccttcctt tctcgccacg ttcgccggct ttccccgtca     5280
agctctaaat cgggggctcc ctttagggtt ccgatttagt gctttacggc acctcgaccc     5340
caaaaaactt gatttgggtg atggttcacg tagtgggcca tcgccctgat agacggtttt     5400
tcgccctttg acgttggagt ccacgttctt taatagtgga ctcttgttcc aaactggaac     5460
aacactcaac tctatctcgg gctattcttt tgatttataa gggattttgc cgatttcggt     5520
ctattggtta aaaaatgagc tgatttaaca aaaatttaac gcgaatttta acaaaatatt     5580
aacgtttaca attttatggt gcactctcag tacaatctgc tctgatgccg catagttaag     5640
ccagccccga cacccgccaa cacccgctga cgcgccctga cgggcttgtc tgctcccggc     5700
atccgcttac agacaagctg tgaccgtctc cgggagctgc atgtgtcaga ggttttcacc     5760
gtcatcaccg aaacgcgcga gacgaaaggg cctcgtgata cgcctatttt tataggttaa     5820
tgtcatgata ataatggttt cttagacgtc aggtggcact tttcggggaa atgtgcgcgg     5880
aacccctatt tgtttatttt tctaaataca ttcaaatatg tatccgctca tgagacaata     5940
accctgataa atgcttcaat aatattgaaa aaggaagagt atgagtattc aacatttccg     6000
tgtcgccctt attcccttttt ttgcggcatt ttgccttcct gttttttgctc acccagaaac     6060 gctggtgaaa gtaaaagatg ctgaagatca gttgggtgca cgagtgggtt acatcgaact     6120
ggatctcaac agcggtaaga tccttgagag ttttcgcccc gaagaacgtt ttccaatgat     6180
gagcactttt aaagttctgc tatgtggcgc ggtattatcc cgtattgacg ccgggcaaga     6240
gcaactcggt cgccgcatac actattctca gaatgacttg gttgagtact caccagtcac     6300
agaaaagcat cttacggatg gcatgacagt aagagaatta tgcagtgctg ccataaccat     6360
gagtgataac actgcggcca acttacttct gacaacgatc ggaggaccga aggagctaac     6420
cgcttttttg cacaacatgg gggatcatgt aactcgcctt gatcgttggg aaccggagct     6480
gaatgaagcc ataccaaacg acgagcgtga caccacgatg cctgtagcaa tggcaacaac     6540
gttgcgcaaa ctattaactg gcgaactact tactctagct tcccggcaac aattaataga     6600
ctggatggag gcggataaag ttgcaggacc acttctgcgc tcggcccttc cggctggctg     6660
gtttattgct gataaatctg gagccggtga gcgtggaagc cgcggtatca ttgcagcact     6720
ggggccagat ggtaagccct cccgtatcgt agttatctac acgacgggga gtcaggcaac     6780
tatggatgaa cgaaatagac agatcgctga taggtgcc tcactgatta agcattggta     6840
actgtcagac caagtttact catatatact ttagattgat ttaaaacttc atttttaatt     6900
taaaaggatc taggtgaaga tcctttttga atctcatg accaaaatcc cttaacgtga     6960
gttttcgttc cactgagcgt cagaccccgt agaaaagatc aaaggatctt cttgagatcc     7020 ttttttttctg cgcgtaatct gctgcttgca acaaaaaaa ccaccgctac cagcggtggt     7080
ttgtttgccg gatcaagagc taccaactct ttttccgaag gtaactggct tcagcagagc     7140
gcagatacca aatactgttc ttctagtgta gccgtagtta ggccaccact tcaagaactc     7200
tgtagcaccg cctacatacc tcgctctgct aatcctgtta ccagtggctg ctgccagtgg     7260
cgataagtcg tgtcttaccg ggttggactc aagacgatag ttaccggata aggcgcagcg     7320
gtcgggctga acggggggtt cgtgcacaca gcccagcttg gagcgaacga cctacaccga     7380
actgagatac ctacagcgtg agctatgaga aagcgccacg cttcccgaag ggagaaaggc     7440
ggacaggtat ccggtaagcg gcagggtcgg aacaggagag cgcacgaggg agcttccagg     7500
```

-continued

```
gggaaacgcc tggtatcttt atagtcctgt cgggtttcgc cacctctgac ttgagcgtcg    7560
atttttgtga tgctcgtcag gggggcggag cctatggaaa aacgccagca acgcggcctt    7620
tttacggttc ctggcctttt gctggccttt tgctcacatg t                        7661

<210> SEQ ID NO 4
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA targeting Dmd-E4 mouse mutation site

<400> SEQUENCE: 4
cattattttt ctgtaagacc                                                 20

<210> SEQ ID NO 5
<211> LENGTH: 5895
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Sequence of AAV vector plasmid expressing sgRNA
      targeting Dmd-E4 mouse mutation site

<400> SEQUENCE: 5
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
aggggttcct gcggcctcta gactcgagga gggcctattt cccatgattc cttcatattt    180
gcatatacga tacaaggctg ttagagagat aattagaatt aatttgactg taaacacaaa    240
gatattagta caaaatacgt gacgtagaaa gtaataattt cttgggtagt ttgcagtttt    300
aaaattatgt tttaaaatgg actatcatat gcttaccgta acttgaaagt atttcgattt    360
cttggcttta tatatcttgt ggaaaggacg aaacaccgca ttattttct gtaagaccgt    420 tatagtactc tggaaacaga atctactata acaaggcaaa atgccgtgtt tatctcgtca    480
acttgttggc gagattttttt tttttttct agacccagct ttcttgtaca aagttggcat    540
tagctagcgc taaccggtgg cgcgttaagt cgacgaacgc tgacgtcatc aacccgctcc    600
aaggaatcgc gggcccagtg tcactaggcg ggaacaccca gcgcgcgtgc gccctggcag    660
gaagatggct gtgagggaca ggggagtggc gccctgcaat atttgcatgt cgctatgtgt    720
tctgggaaat caccataaac gtgaaatgtc tttggatttg ggaatcttat aagttctgta    780
tgagaccaca gatctgacat tattttttctg taagaccgtt atagtactct ggaaacagaa    840
tctactataa caaggcaaaa tgccgtgttt atctcgtcaa cttgttggcg agattttttt    900
tttttctaga cccagctttc ttgtacaaag ttggcattaa agcttatcga taccctgcag    960
tatttagcat gccccaccca tctgcaaggc attctggata gtgtcaaaac agccggaaat    1020
caagtccgtt tatctcaaac tttagcattt gggaataaaa tgatatttgc tatgctggtt    1080
aaattagatt ttagttaaat ttcctgctga agctctagta cgataagtaa cttgacctaa    1140
gtgtaaagtt gagatttcct tcaggtttat atagcttgtg cgccgcctgg gtaccagatc    1200
tgacattatt tttctgtaag accgttatag tactctggaa acagaatcta ctataacaag    1260
gcaaaatgcc gtgtttatct cgtcaacttg ttggcgagat tttttttttt ttctagaccc    1320
```

-continued

```
agctttcggt actcgcggcc gccggccgtc cgccctcggc accattcctc acgacaccga   1380
aatatggcga cgggtgagga atggtgggga gttattttta gagcggtgag gaatggtggg   1440
caggcagcag gtgttggggg agttatttt agagcgggga gttattttta gagcggtgag   1500
gaatggtgga caccgaaata tggcgacggg tgaggaatgg tgccgtcgcc atatttgggt   1560
gtcccgtccg ccctcggccg gggccgcatt cctgggggcc gggcggtgct cccgcccgcc   1620
tcgataaaag gctccggggc cggcggcggc ccacgagcta cccggaggag cgggaggcgt   1680
ctctgccagc ggtccgacgc gcagtcagca ccaggtaggt gggcaccgcg ccgtgccgtg   1740
ccctctggct aactaccatg gtgagcaagg gcgaggagct gttcaccggg gtggtgccca   1800
tcctggtcga gctggacggc gacgtaaacg gccacaagtt cagcgtgtct ggcgagggcg   1860
agggcgatgc cacctacggc aagctgaccc tgaagttcat ctgcaccacc ggcaagctgc   1920
ccgtgccctg gcccaccctc gtgaccaccc tgacctacgg cgtgcagtgc ttcagccgct   1980
accccgacca catgaagcag cacgacttct tcaagtccgc catgcccgaa ggctacgtcc   2040
aggagcgcac catcttcttc aaggacgacg gcaactacaa gacccgcgcc gaggtgaagt   2100
tcgagggcga cacccctggtg aaccgcatcg agctgaaggg catcgacttc aaggaggacg   2160
gcaacatcct ggggcacaag ctggagtaca actacaacag ccacaacgtc tatatcatgg   2220
ccgacaagca gaagaacggc atcaaggcga acttcaagat ccgccacaac atcgaggacg   2280
gcagcgtgca gctcgccgac cactaccagc agaacacccc catcggcgac ggccccgtgc   2340
tgctgcccga caaccactac ctgagcaccc agtccgccct gagcaaagac cccaacgaga   2400
agcgcgatca catggtcctg ctggagttcg tgaccgccgc cgggatcact ctcggcatgg   2460
acgagctgta caagtgcgca acaaacttct ctctgctgaa acaagccgga gatgtcgaag   2520
agaatcctgg accccactaat ctgtcagata ttattgaaaa ggagaccggt aagcaactgg   2580
ttatccagga atccatcctc atgctcccag aggaggtgga agaagtcatt gggaacaagc   2640
cggaaagcga tatactcgtg cacaccgcct acgacgagag caccgacgag aatgtcatgc   2700
ttctgactag cgacgcccct gaatacaagc cttgggctct ggtcatacag gatagcaacg   2760
gtgagaacaa gattaagatg ctctctggtg gttctcccaa gaagaagagg aaagtcggat   2820
cctacccata cgatgttcca gattacgctt acccatacga tgttccagat tacgcttacc   2880
catacgatgt tccagattac gcttaagaat tcctagagct cgctgatcag cctcgactgt   2940
gccttctagt tgccagccat ctgttgtttg cccctccccc gtgccttcct tgaccctgga   3000
aggtgccact cccactgtcc tttcctaata aaatgaggaa attgcatcgc attgtctgag   3060
taggtgtcat tctattctgg ggggtggggt ggggcaggac agcaagggg aggattggga   3120 agagaatagc aggcatgctg gggaggaatt cggccgcagg aacccctagt gatggagttg   3180
gccactccct ctctgcgcgc tcgctcgctc actgaggccg ggcgaccaaa ggtcgcccga   3240
cgcccgggct ttgcccgggc ggcctcagtg agcgagcgag cgcgcagctg cctgcagggg   3300
cgcctgatgc ggtattttct ccttacgcat ctgtgcggta tttcacaccg catacgtcaa   3360
agcaaccata gtacgcgccc tgtagcggcg cattaagcgc ggcgggtgtg tggttacgc   3420 gcagcgtgac cgctacactt gccagcgcct tagcgcccgc tcctttcgct ttcttccctt   3480
cctttctcgc cacgttcgcc ggctttcccc gtcaagctct aaatcggggg ctccctttag   3540
ggttccgatt tagtgcttta cggcacctcg acccccaaaa acttgatttg ggtgatggtt   3600
cacgtagtgg gccatcgccc tgatagacgg tttttcgccc tttgacgttg gagtccacgt   3660
tctttaatag tggactcttg ttccaaactg gaacaacact caactctatc tcgggctatt   3720
```

-continued

```
cttttgattt ataagggatt ttgccgattt cggtctattg gttaaaaaat gagctgattt    3780
aacaaaaatt taacgcgaat tttaacaaaa tattaacgtt tacaatttta tggtgcactc    3840
tcagtacaat ctgctctgat gccgcatagt taagccagcc ccgacacccg ccaacacccg    3900
ctgacgcgcc ctgacgggct tgtctgctcc cggcatccgc ttacagacaa gctgtgaccg    3960
tctccgggag ctgcatgtgt cagaggtttt caccgtcatc accgaaacgc gcgagacgaa    4020
agggcctcgt gatacgccta ttttttatagg ttaatgtcat gataataatg gtttcttaga   4080
cgtcaggtgg cacttttcgg ggaaatgtgc gcggaacccc tatttgttta tttttctaaa    4140
tacattcaaa tatgtatccg ctcatgagac aataaccctg ataaatgctt caataatatt    4200
gaaaaaggaa gagtatgagt attcaacatt tccgtgtcgc ccttattccc ttttttgcgg    4260
cattttgcct tcctgttttt gctcacccag aaacgctggt gaaagtaaaa gatgctgaag    4320
atcagttggg tgcacgagtg ggttacatcg aactggatct caacagcggt aagatccttg    4380
agagttttcg ccccgaagaa cgttttccaa tgatgagcac ttttaaagtt ctgctatgtg    4440
gcgcggtatt atcccgtatt gacgccgggc aagagcaact cggtcgccgc atacactatt    4500
ctcagaatga cttggttgag tactcaccag tcacagaaaa gcatcttacg gatggcatga    4560
cagtaagaga attatgcagt gctgccataa ccatgagtga taacactgcg gccaacttac    4620
ttctgacaac gatcggagga ccgaaggagc taaccgcttt tttgcacaac atggggggatc    4680 atgtaactcg ccttgatcgt tgggaaccgg agctgaatga agccatacca aacgacgagc    4740
gtgacaccac gatgcctgta gcaatggcaa caacgttgcg caaactatta actggcgaac    4800
tacttactct agcttcccgg caacaattaa tagactggat ggaggcggat aaagttgcag    4860
gaccacttct gcgctcggcc cttccggctg gctggtttat tgctgataaa tctggagccg    4920
gtgagcgtgg aagccgcggt atcattgcag cactggggcc agatggtaag ccctcccgta    4980
tcgtagttat ctacacgacg gggagtcagg caactatgga tgaacgaaat agacagatcg    5040
ctgagatagg tgcctcactg attaagcatt ggtaactgtc agaccaagtt tactcatata    5100
tactttagat tgatttaaaa cttcattttt aatttaaaag gatctaggtg aagatccttt    5160
ttgataatct catgaccaaa atcccttaac gtgagttttc gttccactga gcgtcagacc    5220
ccgtagaaaa gatcaaagga tcttcttgag atcctttttt tctgcgcgta atctgctgct    5280
tgcaaacaaa aaaaccaccg ctaccagcgg tggtttgttt gccggatcaa gagctaccaa    5340
ctctttttcc gaaggtaact ggcttcagca gagcgcagat accaaatact gttcttctag    5400
tgtagccgta gttaggccac cacttcaaga actctgtagc accgcctaca tacctcgctc    5460
tgctaatcct gttaccagtg gctgctgcca gtggcgataa gtcgtgtctt accgggttgg    5520
actcaagacg atagttaccg gataaggcgc agcggtcggg ctgaacgggg ggttcgtgca    5580
cacagcccag cttggagcga acgacctaca ccgaactgag atacctacag cgtgagctat    5640
gagaaagcgc cacgcttccc gaagggagaa aggcggacag gtatccggta agcggcaggg    5700
tcggaacagg agagcgcacg agggagcttc caggggggaaa cgcctggtat ctttatagtc    5760
ctgtcgggtt tcgccacctc tgacttgagc gtcgattttt gtgatgctcg tcagggggggc    5820 ggagcctatg gaaaaacgcc agcaacgcgg cctttttacg gttcctggcc ttttgctggc    5880
cttttgctca catgt                                                     5895
```

<210> SEQ ID NO 6
<211> LENGTH: 5067
<212> TYPE: DNA

-continued

<213> ORGANISM: Artificial Sequence
<220> FEATURE:
<223> OTHER INFORMATION: synthesized
<220> FEATURE:
<221> NAME/KEY: misc_feature
<223> OTHER INFORMATION: The corresponding sequence comprising AID-Cas9
      fusion protein and sgRNA targeting Dmd-E4 mouse in the one AAV
      vector plasmid

<400> SEQUENCE: 6

```
gcggcctcta gactcgagcg gccgtccgcc ctcggcacca ttcctcacga caccgaaata     60
tggcgacggg tgaggaatgg tggggagtta tttttagagc ggtgaggaat ggtgggcagg    120
cagcaggtgt tggggagtt attttttagag cggggagtta tttttagagc ggtgaggaat    180
ggtggacacc gaaatatggc gacgggtgag gaatggtgcc gtcgccatat ttgggtgtcc    240
cgtccgccct cggccggggc cgcattcctg ggggccgggc ggtgctcccg cccgcctcga    300
taaaaggctc cggggccggc ggcggcccac gagctacccg gaggagcggg aggcgtctct    360
gccagcggtc cgacgcgcag tcagcaccag gtaggtgggc accgcgccgt gccgtgccgc    420
tagctaatac gactcactat agggagagcc gccaccatgg actataagga ccacgacgga    480
gactacaagg atcatgatat tgattacaaa gacgatgacg ataagatggc cccaaagaag    540
aagcggaagg tcggtatcca cggagtccca gcagccatgg acagcctctt gatgaaccgg    600
agggagtttc tttaccaatt caaaaatgtc cgctgggcta agggtcggcg tgagacctac    660
ctgtgctacg tagtgaagag gcgtgacagt gctacatcct tttcactgga ctttggttat    720
cttcgcaata agaacggctg ccacgtggaa ttgctcttcc tccgctacat ctcggactgg    780
gacctagacc ctggccgctg ctaccgcgtc acctggttca tctcctggag ccctgctac    840 gactgtgccc gacatgtggc cgactttctg cgagggaacc ccaacctcag tctgaggatc    900
ttcaccgcgc gcctctactt ctgtgaggac cgcaaggctg agcccgaggg gctgcggcgg    960
ctgcaccgcg ccgggggtgca aatagccatc atgaccttca aagattattt ttactgctgg   1020 aatactttttg tagaaaacca tggaagaact ttcaaagcct gggaagggct gcatgaaaat   1080
tcagttcgtc tatccagaca gcttcggcgc atccttttgc ccagcggcag cgagactccc   1140
gggacctcag agtccgccac acccgaaagc ggcaagagga actacatcct gggcctggcc   1200
atcggcatca ccagcgtggg ctacggcatc atcgactacg agaccaggga cgtgatcgac   1260
gccggcgtga ggctgttcaa ggaggccaac gtggagaaca cgagggcag gaggagcaag   1320 aggggcgcca ggaggctgaa gaggaggagg aggcacagga tccagagggt gaagaagctg   1380
ctgttcgact acaacctgct gaccgaccac agcgagctga gcggcatcaa cccttacgag   1440
gccagggtga agggcctgag ccagaagctg agcgaggagg agttcagcgc cgccctgctg   1500
cacctggcca agaggagggg cgtgcacaac gtgaacgagg tggaggagga caccggcaac   1560
gagctgagca ccaaggagca gatcagcagg aacagcaagg ccctggagga agtacgtg    1620 gccgagctgc agctggagag gctgaagaag gacggcgagg tgaggggcag catcaacagg   1680
ttcaagacca gcgactacgt gaaggaggcc aagcagctgc tgaaggtgca gaaggcctac   1740
caccagctgg accagagctt catcgacacc tacatcgacc tgctggagac caggaggacc   1800
tactacgagg gccctggcga gggcagccct ttcggctgga aggacatcaa ggagtggtac   1860
gagatgctga tgggccactg cacctacttc cctgaggagc tgaggagcgt gaagtacgcc   1920
tacaacgccg acctgtacaa cgccctgaac gacctgaaca acctggtgat caccaggac    1980 gagaacgaga agctggagta ctacgagaag ttccagatca tcgagaacgt gttcaagcag   2040
```

-continued

```
aagaagaagc ctaccctgaa gcagatcgcc aaggagatcc tggtgaacga ggaggacatc    2100
aagggctaca gggtgaccag caccggcaag cctgagttca ccaacctgaa ggtgtaccac    2160
gacatcaagg acatcaccgc caggaaggag atcatcgaga acgccgagct gctggaccag    2220
atcgccaaga tcctgaccat ctaccagagc agcgaggaca tccaggagga gctgaccaac    2280
ctgaacagcg agctgaccca ggaggagatc gagcagatca gcaacctgaa gggctacacc    2340
ggcacccaca acctgagcct gaaggccatc aacctgatcc tggacgagct gtggcacacc    2400
aacgacaacc agatcgccat cttcaacagg ctgaagctgg tgcctaagaa ggtggacctg    2460
agccagcaga aggagatccc taccaccctg gtggacgact tcatcctgag ccctgtggtg    2520
aagaggagct tcatccagag catcaaggtg atcaacgcca tcatcaagaa gtacggcctg    2580
cctaacgaca tcatcatcga gctggccagg gagaagaaca gcaaggacgc ccagaagatg    2640
atcaacgaga tgcagaagag gaacaggcag accaacgaga ggatcgagga gatcatcagg    2700
accaccggca aggagaacgc caagtacctg atcgagaaga tcaagctgca cgacatgcag    2760
gagggcaagt gcctgtacag cctggaggcc atccctctgg aggacctgct gaacaaccct    2820
ttcaactacg aggtggacca catcatccct aggagcgtga gcttcgacaa cagcttcaac    2880
aacaaggtgc tggtgaagca ggaggagaac agcaagaagg gcaacaggac ccctttccag    2940
tacctgagca gcagcgacag caagatcagc tacgagacct tcaagaagca catcctgaac    3000
ctggccaagg gcaagggcag gatcagcaag accaagaagg agtacctgct ggaggagagg    3060
gacatcaaca ggttcagcgt gcagaaggac ttcatcaaca ggaacctggt ggacaccagg    3120
tacgccacca ggggcctgat gaacctgctg aggagctact tcagggtgaa caacctggac    3180
gtgaaggtga gagcatcaa cggcggcttc accagcttcc tgaggaggaa gtggaagttc    3240
aagaaggaga ggaacaaggg ctacaagcac cacgccgagg acgccctgat catcgccaac    3300
gccgacttca tcttcaagga gtggaagaag ctggacaagg ccaagaaggt gatggagaac    3360
cagatgttcg aggagaagca ggccgagagc atgcctgaga tcgagaccga gcaggagtac    3420
aaggagatct tcatcacccc ctcaccagatc aagcacatca aggacttcaa ggactacaag    3480
tacagccaca gggtggacaa gaagcctaac aggaagctga tcaacgacac cctgtacagc    3540
accaggaagg acgacaaggg caacaccctg atcgtgaaca acctgaacgg cctgtacgac    3600
aaggacaacg acaagctgaa gaagctgatc aacaagagcc ctgagaagct gctgatgtac    3660
caccacgacc ctcagaccta ccagaagctg aagctgatca tggagcagta cggcgacgag    3720
aagaaccctc tgtacaagta ctacgaggag accggcaact acctgaccaa gtacagcaag    3780
aaggacaacg gccctgtgat caagaagatc aagtactacg gcaacaagct gaacgcccac    3840
ctggacatca ccgacgacta ccctaacagc aggaacaagg tggtgaagct gagcctgaag    3900
ccttacaggt tcgacgtgta cctggacaac ggcgtgtaca agttcgtgac cgtgaagaac    3960
ctggacgtga tcaagaagga gaactactac gaggtgaaca gcaagtgcta cgaggaggcc    4020
aagaagctga gaagatcag caaccaggcc gagttcatcg ccagcttcta caagaacgac    4080
ctgatcaaga tcaacggcga gctgtacagg gtgatcggcg tgaacaacga cctgctgaac    4140
aggatcgagg tgaacatgat cgacatcacc tacagggagt acctggagaa catgaacgac    4200
aagaggcctc tccacatcat caagaccatc gccagcaaga cccagagcat caagaagtac    4260
agcaccgaca tcctgggcaa cctgtacgag gtgaagagca gaagcacccc tcagatcatc    4320
aagaagggcg gcagcagcgg cggcagcacc aacctgagcg acatcatcga gaaggagacc    4380
ggtaagcaac tggttatcca ggaatccatc ctcatgctcc cagaggaggt ggaagaagtc    4440
```

-continued

```
attgggaaca agccggaaag cgatatactc gtgcacaccg cctacgacga gagcaccgac    4500
gagaatgtca tgcttctgac tagcgacgcc cctgaataca agccttgggc tctggtcata    4560
caggatagca acggtgagaa caagattaag atgctctctg gtggttctcc caagaagaag    4620
aggaaagtct aatagcaata aaggatcgtt tattttcatt ggaagcgtgt gttggttttt    4680
tgatcaggcg cggagggcct atttcccatg attccttcat atttgcatat acgatacaag    4740
gctgttagag agataaattag aattaatttg actgtaaaca caaagatatt agtacaaaat    4800
acgtgacgta gaaagtaata atttcttggg tagtttgcag ttttaaaatt atgtttaaa    4860 atggactatc atatgcttac cgtaacttga aagtatttcg atttcttggc tttatatatc    4920
ttgtggaaag gacgaaacac cgcattattt ttctgtaaga ccgttatagt actctggaaa    4980
cagaatctac tataacaagg caaaatgccg tgtttatctc gtcaacttgt tggcgagatt    5040
tttttttttt ttctagaccg cggccgc                                         5067
```

```
<210> SEQ ID NO 7
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA targeting the human DMD gene Exon50

<400> SEQUENCE: 7
acttacaggc tccaatagtg                                                  20

<210> SEQ ID NO 8
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-1 targeting the human DMD gene Exon51

<400> SEQUENCE: 8
gtaacagtct gagtaggagc                                                  20

<210> SEQ ID NO 9
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-2 targeting the human DMD gene Exon51

<400> SEQUENCE: 9
tgtgtcacca gagtaacagt                                                  20

<210> SEQ ID NO 10
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-3 targeting the human DMD gene Exon51
```

<400> SEQUENCE: 10
gtaaccacag gttgtgtcac                                                                                   20

<210> SEQ ID NO 11
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-4 targeting the human DMD gene Exon51

<400> SEQUENCE: 11
gctcctactc agactgttac                                                                                   20

<210> SEQ ID NO 12
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-5 targeting the human DMD gene Exon51

<400> SEQUENCE: 12
gttactctgg tgacacaacc                                                                                   20

<210> SEQ ID NO 13
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-6 targeting the human DMD gene Exon51

<400> SEQUENCE: 13
tggcagtttc cttagtaacc                                                                                   20

<210> SEQ ID NO 14
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-7 targeting the human DMD gene Exon51

<400> SEQUENCE: 14
caggtacctc caacatcaag                                                                                   20

<210> SEQ ID NO 15
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-8 targeting the human DMD gene Exon51

<400> SEQUENCE: 15
gaaactgcca tctccaaact                                                                                   20

```
<210> SEQ ID NO 16
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-9 targeting the human DMD gene Exon51

<400> SEQUENCE: 16
tgatcaagca gagaaagcca                                                   20

<210> SEQ ID NO 17
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-10 targeting the human DMD gene Exon51

<400> SEQUENCE: 17
aacttgatca agcagagaaa                                                   20

<210> SEQ ID NO 18
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-11 targeting the human DMD gene Exon51

<400> SEQUENCE: 18
aaggtatgag aaaaaatgat                                                   20

<210> SEQ ID NO 19
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-12 targeting the human DMD gene Exon51
      acaggttgtgtcaccagagt

<400> SEQUENCE: 19
acaggttgtg tcaccagagt                                                   20

<210> SEQ ID NO 20
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: sgRNA-13 targeting the human DMD gene Exon51

<400> SEQUENCE: 20
aacgagatga tcatcaagca                                                   20

<210> SEQ ID NO 21
<211> LENGTH: 30
```

-continued

```
<212> TYPE: DNA
<213> ORGANISM: Homo sapiens

<400> SEQUENCE: 21
ctgttactct ggtgacacaa cctgtggtta                                    30

<210> SEQ ID NO 22
<211> LENGTH: 30
<212> TYPE: DNA
<213> ORGANISM: Homo sapiens

<400> SEQUENCE: 22
agactgttac tctggtgaca caacctgtgg                                    30

<210> SEQ ID NO 23
<211> LENGTH: 30
<212> TYPE: DNA
<213> ORGANISM: Homo sapiens

<400> SEQUENCE: 23
tcttccttga tgttggaggt acctgctctg                                    30

<210> SEQ ID NO 24
<211> LENGTH: 30
<212> TYPE: DNA
<213> ORGANISM: Homo sapiens

<400> SEQUENCE: 24
atatcaacga gatgatcatc aagcagaagg                                    30
```